United States Patent [19]

Taylor

[11] 4,102,669

[45] Jul. 25, 1978

[54] HERBICIDAL BETA-PHENYL-4-PIPERIDINONES AND -DIHYDROPYRIDINONES

[75] Inventor: Harold Mellon Taylor, Indianapolis, Ind.

[73] Assignee: Eli Lilly and Company, Indianapolis, Ind.

[21] Appl. No.: 825,616

[22] Filed: Aug. 18, 1977

Related U.S. Application Data

[60] Division of Ser. No. 685,409, May 20, 1976, Pat. No. 4,065,290, and a continuation-in-part of Ser. No. 593,095, Jul. 3, 1975, abandoned.

[51] Int. Cl.$^2$ ............................................. A01N 9/22
[52] U.S. Cl. ................................. 71/94; 260/294.8 G; 260/297 Z
[58] Field of Search ......... 71/94; 260/297 Z, 294.8 G

[56] References Cited

U.S. PATENT DOCUMENTS 4,065,290  12/1977  Taylor ..................................... 71/94

OTHER PUBLICATIONS

Chemical Abstracts, vol. 85, abst. No. 46406v (1976) (abst. of German Offen., 2,537,753 to Taylor et al).

*Primary Examiner*—John D. Randolph
*Attorney, Agent, or Firm*—Joseph A. Jones; William E. Maycock

[57] ABSTRACT

A class of 4-piperidinones and corresponding dihydropyridinones having a phenyl substituent at one $\beta$-position, an alkyl, alkenyl or propargyl group at the 1-position and an optional substituent at the other $\beta$-position are broad-spectrum herbicides. The compounds bear a metasubstituent on the phenyl ring, and are particularly suited for use as herbicides in cotton culture.

37 Claims, No Drawings

HERBICIDAL BETA-PHENYL-4-PIPERIDINONES AND -DIHYDROPYRIDINONES

This is a division of application Ser. No. 685,409 filed May 20, 1976, now U.S. Pat. No. 4,065,290 granted Dec. 27, 1977, which was a continuation-in-part of application Ser. No. 593,095, filed Jul. 3, 1975, now abandoned.

BACKGROUND OF THE INVENTION

This invention belongs to the field of agricultural chemistry, and provides to the art new herbicides and herbicidal methods.

It has long been established that herbicides are necessary to the most economical and productive use of the land. Herbicides are in demand for use in killing and controlling weeds growing in cropland, and also for killing and controlling unwanted vegetation of all kinds, such as in fallow land and on industrial property.

Despite the great amount of research effort which has been expended in agricultural chemistry, herbicides closely related to the compounds of this invention have not been previously discovered. The polyhalopyridinones, which have two or more chlorine atoms as well as other alkyl and halo substituents on the pyridine rings, are known herbicides, but are obviously quite distant from the present invention.

Organic chemists have explored the piperidinones and dihydropyridinones to a degree. For example, Leonard et al., J. Am. Chem. Soc. 79, 156-60 (1957), disclosed 3,5-di(substituted-benzyl and benzylidene)-4-piperidinones, which are not herbicides.

Settimj et al. have worked with piperidinones, and have disclosed the unsubstituted 3,5-diphenyl-1-methyl-4-piperidinone. Gazz. Chim. Ital. 96, 604-11 (1966), C.A. 65, 8913g (1966); Gazz. Chim. Ital. 96, 311-24 (1966), C.A. 67, 64261b (1967); Gazz. Chim. Ital. 100, 703-25 (1970), C.A. 74, 41752t (1971).

SUMMARY OF THE INVENTION

A series of 1-substituted β-phenyl-4-piperidinones and -dihydropyridinones are herbicides active against a wide range of weeds. Many of the compounds are new and are here disclosed for the first time. Herbicidal methods and compositions making use of the compounds, which are particularly useful in cotton culture, are also disclosed.

The new compounds of this invention are of one of the formulae

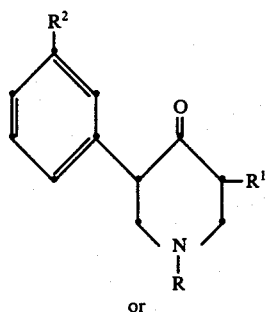

I or

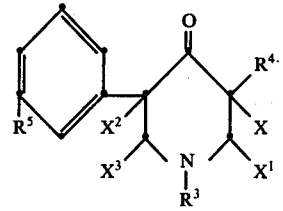

II wherein
R represents methyl or ethyl;
$R^1$ represents hydrogen, phenoxy, phenylthio, $C_1$-$C_4$ alkoxy, $C_1$-$C_4$ alkylthio, $C_1$-$C_4$ alkyl, phenyl or phenyl monosubstituted with chloro or fluoro;
$R^2$ represents bromo, fluoro or trifluoromethyl;
$R^3$ represents $C_1$-$C_3$ alkyl, $C_2$-$C_3$ alkenyl or propargyl;
$R^4$ represents hydrogen, phenoxy, phenylthio, $C_1$-$C_4$ alkyl, $C_1$-$C_4$ alkoxy, $C_1$-$C_4$ alkylthio, phenyl or phenyl monosubstituted with chloro, bromo, fluoro, trifluoromethyl, $C_1$-$C_3$ alkyl or $C_1$-$C_3$ alkoxy;
$R^5$ represents chloro, bromo, fluoro, trifluoromethyl, $C_1$-$C_3$ alkyl or $C_1$-$C_3$ alkoxy;
either X and $X^1$ combine to form a carbon-carbon bond and $X^2$ and $X^3$ represent hydrogen atoms, or X and $X^1$ represent hydrogen atoms and $X^2$ and $X^3$ combine to form a carbon-carbon bond.

The herbicidal methods of this invention are methods of reducing the vigor of unwanted herbaceous plants which comprise contacting the plants with an herbicidally-effective amount of a compound of the formula

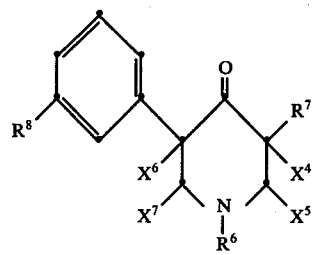

III wherein
$R^6$ represents $C_1$-$C_3$ alkyl, $C_2$-$C_3$ alkenyl or propargyl;
$R^7$ represents hydrogen, phenoxy, phenylthio, $C_1$-$C_4$ alkyl, $C_1$-$C_4$ alkoxy, $C_1$-$C_4$ alkylthio, phenyl or phenyl monosubstituted with chloro, bromo, fluoro, trifluoromethyl, $C_1$-$C_3$ alkyl or $C_1$-$C_3$ alkoxy;
$R^8$ represents chloro, bromo, fluoro, trifluoromethyl, $C_1$-$C_3$ alkyl or $C_1$-$C_3$ alkoxy;
each of $X^4$ and $X^5$ represents hydrogen, or $X^4$ and $X^5$ combine to form a carbon-carbon bond;
each of $X^6$ and $X^7$ represents hydrogen, or $X^6$ and $X^7$ combine to form a carbon-carbon bond;
provided that no more than one of ($X^4$ and $X^5$) and ($X^6$ and $X^7$) form a bond.

The herbicidal compositions of this invention comprise an inert-carrier and an herbicidally-effective amount of a compound described above.

DESCRIPTION OF THE PREFERRED EMBODIMENT

In the above formulae, the general chemical terms are used in their usual meanings in the organic chemical art.

For example, the terms $C_1$-$C_3$ alkoxy, $C_1$-$C_3$ alkyl, $C_1$-$C_4$ alkyl, $C_1$-$C_4$ alkoxy, $C_1$-$C_4$ alkylthio and $C_2$-$C_3$ alkenyl refer to such groups as methoxy, ethoxy, isopropoxy, methylthio, ethylthio, propylthio, methyl, ethyl, propyl, vinyl, allyl, 1-propenyl, butyl, t-butyl, isobutyl, butoxy and isobutylthio.

Agricultural chemists will immediately understand that the addition of commonly-used substituents to the compounds of this invention is expected to produce active compounds equivalent to those explicitly described herein. For example, such substituents as halogen atoms, $C_1$-$C_3$ alkoxy, alkylthio and alkyl groups, and trifluoromethyl groups, as well as functional groups such as hydroxy, alkoxycarbonyl and cyano groups, may be added to the compounds. In particular, the phenoxy and phenylthio $R^1$, $R^4$ and $R^7$ groups may be substituted with such groups, particularly with halogen atoms, methyl and methoxy groups and trifluoromethyl groups, with the expectation of producing piperidinones and dihydropyridinones equivalent to the other compounds described herein.

It will also be understood that acid addition salts of the compounds may be made and used for the control of weeds. For example, such salts as hydrochlorides, hydrobromides, hydrofluorides, sulfates, nitrates, toluenesulfonates, methanesulfonates, trifluoromethanesulfonates and the like are often used in agricultural chemistry. Salts of the present compounds are made in the usual manner by simple contact of the compound with the acid in a solvent such as an aqueous alcohol.

It will be understood that the present invention may be practiced in various ways, making use of different classes of compounds of the present invention. In such manners of practicing the invention, various classes of compounds may be used in carrying out the herbicidal methods, and making use of the herbicidal compositions, of this invention. For example, the following classes of compounds are contemplated, as new compositions in the case of compounds of formulae I and II, and for use in herbicidal methods and compositions in all cases.

(1) Compounds of formula I;
(2) compounds of formula II; compounds of formula I wherein:
(3) $R^1$ represents hydrogen, alkyl, phenyl or substituted phenyl;
(4) $R^1$ represents hydrogen, phenoxy, phenylthio, phenyl or substituted phenyl;
(5) $R^1$ represents phenoxy, phenylthio, phenyl or substituted phenyl;
(6) $R^1$ represents hydrogen, alkyl, alkoxy or alkylthio;
(7) $R^1$ represents alkyl, alkoxy or alkylthio;
(8) $R^1$ represents hydrogen, alkoxy, alkylthio, alkyl, phenyl or substituted phenyl; compounds of formula II wherein:
(9) $R^3$ represents alkyl or alkenyl;
(10) $R^3$ represents alkyl;
(11) $R^3$ represents alkenyl or propargyl;
(12) $R^4$ represents alkyl, phenyl or substituted phenyl;
(13) $R^4$ represents hydrogen, phenoxy, phenylthio, phenyl or substituted phenyl;
(14) $R^4$ represents phenoxy, phenylthio, phenyl or substituted phenyl;
(15) $R^4$ represents hydrogen, alkyl, alkoxy or alkylthio;
(16) $R^4$ represents alkyl, alkoxy or alkylthio;
(17) $R^4$ represents hydrogen, alkyl, phenyl or phenyl monosubstituted with chloro, bromo, fluoro, trifluoromethyl, methyl or methoxy;
(18) $R^5$ represents chloro, bromo, fluoro, trifluoromethyl, methyl or methoxy;
(19) the compounds as described by subparagraphs 9 and 12;
(20) the compounds as described by subparagraphs 9 and 13;
(21) the compounds as described by subparagraphs 9 and 14;
(22) the compounds as described by subparagraphs 9 and 15;
(23) the compounds as described by subparagraphs 9 and 16;
(24) the compounds as described by subparagraphs 9 and 17;
(25) the compounds as described by subparagraphs 10 and 12;
(26) the compounds as described by subparagraphs 10 and 13;
(27) the compounds as described by subparagraphs 10 and 14;
(28) the compounds as described by subparagraphs 10 and 15;
(29) the compounds as described by subparagraphs 10 and 16;
(30) the compounds as described by subparagraphs 10 and 17;
(31) the compounds as described by subparagraphs 11 and 12;
(32) the compounds as described by subparagraphs 11 and 13;
(33) the compounds as described by subparagraphs 11 and 14;
(34) the compounds as described by subparagraphs 11 and 15;
(35) the compounds as described by subparagraphs 11 and 16;
(36) the compounds as described by subparagraphs 11 and 17;
(37) the compounds as described by subparagraphs 9, 12 and 18;
(38) the compounds as described by subparagraphs 9, 13 and 18;
(39) the compounds as described by subparagraphs 9, 14 and 18;
(40) the compounds as described by subparagraphs 9, 15 and 18;
(41) the compounds as described by subparagraphs 9, 16 and 18;
(42) the compounds as described by subparagraphs 9, 17 and 18;
(43) the compounds as described by subparagraphs 10, 12 and 18;
(44) the compounds as described by subparagraphs 10, 13 and 18;
(45) the compounds as described by subparagraphs 10, 14 and 18;
(46) the compounds as described by subparagraphs 10, 15 and 18;
(47) the compounds as described by subparagraphs 10, 16 and 18;
(48) the compounds as described by subparagraphs 10, 17 and 18;
(49) the compounds as described by subparagraphs 11, 12 and 18;

(50) the compounds as described by subparagraphs 11, 13 and 18;
(51) the compounds as described by subparagraphs 11, 14 and 18;
(52) the compounds as described by subparagraphs 11, 15 and 18;
(53) the compounds as described by subparagraphs 11, 16 and 18;
(54) the compounds as described by subparagraphs 11, 17 and 18; herbicidal methods and compositions using compounds of formula III where:
(55) $X^4$, $X^5$, $X^6$ and $X^7$ all represent hydrogen atoms;
(56) one of ($X^4$ and $X^5$) and ($X^6$ and $X^7$) forms a bond;
(57) $R^6$ represents alkyl or alkenyl;
(58) $R^6$ represents alkenyl or propargyl;
(59) $R^6$ represents alkyl;
(60) $R^7$ represents hydrogen, alkyl, phenyl or substituted phenyl;
(61) $R^7$ represents hydrogen, alkyl, phenyl or phenyl monosubstituted with chloro, bromo, fluoro, trifluoromethyl, methyl or methoxy;
(62) $R^7$ represents hydrogen, phenoxy, phenylthio, phenyl or substituted phenyl;
(63) $R^7$ represents phenoxy, phenylthio, phenyl or substituted phenyl;
(64) $R^7$ represents hydrogen, alkyl, alkoxy or alkylthio;
(65) $R^7$ represents alkyl, alkoxy or alkylthio;
(66) $R^7$ represents alkyl, phenyl, or phenyl substituted with chloro or fluoro;
(67) $R^8$ represents chloro, bromo, fluoro, trifluoromethyl, methyl or methoxy;
(68) the compounds as described by subparagraphs 55 and 57;
(69) the compounds as described by subparagraphs 55 and 58;
(70) the compounds as described by subparagraphs 55 and 59;
(71) the compounds as described by subparagraphs 56 and 57;
(72) the compounds as described by subparagraphs 56 and 58;
(73) the compounds as described by subparagraphs 56 and 59;
(74) the compounds as described by subparagraphs 55 and 67;
(75) the compounds as described by subparagraphs 56 and 67;
(76) the compounds as described by subparagraphs 55 and 60;
(77) the compounds as described by subparagraphs 55 and 61;
(78) the compounds as described by subparagraphs 55 and 62;
(79) the compounds as described by subparagraphs 55 and 63;
(80) the compounds as described by subparagraphs 55 and 64;
(81) the compounds as described by subparagraphs 55 and 65;
(82) the compounds as described by subparagraphs 55 and 66;
(83) the compounds as described by subparagraphs 56 and 60;
(84) the compounds as described by subparagraphs 56 and 61;
(85) the compounds as described by subparagraphs 56 and 62;
(86) the compounds as described by subparagraphs 56 and 63;
(87) the compounds as described by subparagraphs 56 and 64;
(88) the compounds as described by subparagraphs 56 and 65;
(89) the compounds as described by subparagraphs 56 and 66;
(90) the compounds as described by subparagraphs 57 and 60;
(91) the compounds as described by subparagraphs 57 and 61;
(92) the compounds as described by subparagraphs 57 and 62;
(93) the compounds as described by subparagraphs 57 and 63;
(94) the compounds as described by subparagraphs 57 and 64;
(95) the compounds as described by subparagraphs 57 and 65;
(96) the compounds as described by subparagraphs 57 and 66;
(97) the compounds as described by subparagraphs 58 and 60;
(98) the compounds as described by subparagraphs 58 and 61;
(99) the compounds as described by subparagraphs 58 and 62;
(100) the compounds as described by subparagraphs 58 and 63;
(101) the compounds as described by subparagraphs 58 and 64;
(102) the compounds as described by subparagraphs 58 and 65;
(103) the compounds as described by subparagraphs 58 and 66;
(104) the compounds as described by subparagraphs 59 and 60;
(105) the compounds as described by subparagraphs 59 and 61;
(106) the compounds as described by subparagraphs 59 and 62;
(107) the compounds as described by subparagraphs 59 and 63;
(108) the compounds as described by subparagraphs 59 and 64;
(109) the compounds as described by subparagraphs 59 and 65;
(110) the compounds as described by subparagraphs 59 and 66;
(111) the compounds as described by subparagraphs 57 and 67;
(112) the compounds as described by subparagraphs 58 and 67;
(113) the compounds as described by subparagraphs 59 and 67;
(114) the compounds as described by subparagraphs 60 and 67;
(115) the compounds as described by subparagraphs 61 and 67;
(116) the compounds as described by subparagraphs 62 and 67;
(117) the compounds as described by subparagraphs 63 and 67;
(118) the compounds as described by subparagraphs 64 and 67;
(119) the compounds as described by subparagraphs 65 and 67;

(120) the compounds as described by subparagraphs 66 and 67;
(121) the compounds as described by subparagraphs 55, 57 and 60;
(122) the compounds as described by subparagraphs 55, 57 and 61;
(123) the compounds as described by subparagraphs 55, 57 and 62;
(124) the compounds as described by subparagraphs 55, 57 and 63;
(125) the compounds as described by subparagraphs 55, 57 and 64;
(126) the compounds as described by subparagraphs 55, 57 and 65;
(127) the compounds as described by subparagraphs 55, 57 and 66;
(128) the compounds as described by subparagraphs 55, 58 and 60;
(129) the compounds as described by subparagraphs 55, 58 and 61;
(130) the compounds as described by subparagraphs 55, 58 and 62;
(131) the compounds as described by subparagraphs 55, 58 and 63;
(132) the compounds as described by subparagraphs 55, 58 and 64;
(133) the compounds as described by subparagraphs 55, 58 and 65;
(134) the compounds as described by subparagraphs 55, 58 and 66;
(135) the compounds as described by subparagraphs 55, 59 and 60;
(136) the compounds as described by subparagraphs 55, 59 and 61;
(137) the compounds as described by subparagraphs 55, 59 and 62;
(138) the compounds as described by subparagraphs 55, 59 and 63;
(139) the compounds as described by subparagraphs 55, 59 and 64;
(140) the compounds as described by subparagraphs 55, 59 and 65;
(141) the compounds as described by subparagraphs 55, 59 and 66;
(142) the compounds as described by subparagraphs 56, 57 and 60;
(143) the compounds as described by subparagraphs 56, 57 and 61;
(144) the compounds as described by subparagraphs 56, 57 and 62;
(145) the compounds as described by subparagraphs 56, 57 and 63;
(146) the compounds as described by subparagraphs 56, 57 and 64;
(147) the compounds as described by subparagraphs 56, 57 and 65;
(148) the compounds as described by subparagraphs 56, 57 and 66;
(149) the compounds as described by subparagraphs 56, 58 and 60;
(150) the compounds as described by subparagraphs 56, 58 and 61;
(151) the compounds as described by subparagraphs 56, 58 and 62;
(152) the compounds as described by subparagraphs 56, 58 and 63;
(153) the compounds as described by subparagraphs 56, 58 and 64;
(154) the compounds as described by subparagraphs 56, 58 and 65;
(155) the compounds as described by subparagraphs 56, 58 and 66;
(156) the compounds as described by subparagraphs 56, 59 and 60;
(157) the compounds as described by subparagraphs 56, 59 and 61;
(158) the compounds as described by subparagraphs 56, 59 and 62;
(159) the compounds as described by subparagraphs 56, 59 and 63;
(160) the compounds as described by subparagraphs 56, 59 and 64;
(161) the compounds as described by subparagraphs 56, 59 and 65;
(162) the compounds as described by subparagraphs 56, 59 and 66;
(163) the compounds as described by subparagraphs 55, 57, 60 and 67;
(164) the compounds as described by subparagraphs 55, 57, 61 and 67;
(165) the compounds as described by subparagraphs 55, 57, 62 and 67;
(166) the compounds as described by subparagraphs 55, 57, 63 and 67;
(167) the compounds as described by subparagraphs 55, 57, 64 and 67;
(168) the compounds as described by subparagraphs 55, 57, 65 and 67;
(169) the compounds as described by subparagraphs 55, 57, 66 and 67;
(170) the compounds as described by subparagraphs 55, 58, 60 and 67;
(171) the compounds as described by subparagraphs 55, 58, 61 and 67;
(172) the compounds as described by subparagraphs 55, 58, 62 and 67;
(173) the compounds as described by subparagraphs 55, 58, 63 and 67;
(174) the compounds as described by subparagraphs 55, 58, 64 and 67;
(175) the compounds as described by subparagraphs 55, 58, 65 and 67;
(176) the compounds as described by subparagraphs 55, 58, 66 and 67;
(177) the compounds as described by subparagraphs 55, 59, 60 and 67;
(178) the compounds as described by subparagraphs 55, 59, 61 and 67;
(179) the compounds as described by subparagraphs 55, 59, 62 and 67;
(180) the compounds as described by subparagraphs 55, 59, 63 and 67;
(181) the compounds as described by subparagraphs 55, 59, 64 and 67;
(182) the compounds as described by subparagraphs 55, 59, 65 and 67;
(183) the compounds as described by subparagraphs 55, 59, 66 and 67;
(184) the compounds as described by subparagraphs 56, 57, 60 and 67;
(185) the compounds as described by subparagraphs 56, 57, 61 and 67;
(186) the compounds as described by subparagraphs 56, 57, 62 and 67;
(187) the compounds as described by subparagraphs 56, 57, 63 and 67;

(188) the compounds as described by subparagraphs 56, 57, 64 and 67;
(189) the compounds as described by subparagraphs 56, 57, 65 and 67;
(190) the compounds as described by subparagraphs 56, 57, 66 and 67;
(191) the compounds as described by subparagraphs 56, 58, 60 and 67;
(192) the compounds as described by subparagraphs 56, 58, 61 and 67;
(193) the compounds as described by subparagraphs 56, 58, 62 and 67;
(194) the compounds as described by subparagraphs 56, 58, 63 and 67;
(195) the compounds as described by subparagraphs 56, 58, 64 and 67;
(196) the compounds as described by subparagraphs 56, 58, 65 and 67;
(197) the compounds as described by subparagraphs 56, 58, 66 and 67;
(198) the compounds as described by subparagraphs 56, 59, 60 and 67;
(199) the compounds as described by subparagraphs 56, 59, 61 and 67;
(200) the compounds as described by subparagraphs 56, 59, 62 and 67;
(201) the compounds as described by subparagraphs 56, 59, 63 and 67;
(202) the compounds as described by subparagraphs 56, 59, 64 and 67;
(203) the compounds as described by subparagraphs 56, 59, 65 and 67;
(204) the compounds as described by subparagraphs 56, 59, 66 and 67.

In order to assure that agricultural chemists understand and can obtain the compounds of this invention, a number of compounds typical of the invention will be named.

2,3-dihydro-3-(3-methylphenyl)-5-phenyl-1-vinyl-4(1H)-pyridinone
2,3-dihydro-1-ethyl-3,5-bis(3-methylphenyl)-4(1H)-pyridinone
3-(2-chlorophenyl)-5-(3-chlorophenyl)-2,3-dihydro-1-propargyl-4(1H)-pyridinone
2,3-dihydro-5-(3-fluorophenyl)-3-phenoxy-1-(1-propenyl)-4(1H)-pyridinone
2,3-dihydro-3-(3-ethylphenyl)-1-isopropyl-5-phenylthio-4(1H)-pyridinone
2,3-dihydro-5-(4-methylphenyl)-1-propyl-3-(3-trifluoromethylphenyl)-4(1H)-pyridinone
2,3-dihydro-3-methyl-5-(3-propoxyphenyl)-1-propyl-4(1H)-pyridinone
2,3-dihydro-3-(3-methoxyphenyl)-5-methoxy-1-methyl-4(1H)-pyridinone
5-(3-bromophenyl)-2,3-dihydro-1-ethyl-3-(4-fluorophenyl)-4(1H)-pyridinone
1-allyl-2,3-dihydro-5-(3-ethoxyphenyl)-3-(2-methylphenyl)-4(1H)-pyridinone
2,3-dihydro-5-ethoxy-1-ethyl-3-(3-propylphenyl)-4(1H)-pyridinone
2,3-dihydro-5-(3-isopropylphenyl)-1-methyl-3-propyl-4(1H)-pyridinone
5-(4-bromophenyl)-2,3-dihydro-3-(3-ethoxyphenyl)-1-isopropenyl-4(1H)-pyridinone
5-(3-chlorophenyl)-2,3-dihydro-3-propoxy-1-propyl-4(1H)-pyridinone
2,3-dihydro-5-(3-methoxyphenyl)-1-(1-propenyl)-3-(2-propylphenyl)-4(1H9-pyridinone
2,3-dihydro-5-(3-fluorophenyl)-1-isopropyl-3-(3-trifluoromethylphenyl)-4(1H)-pyridinone
2,3-dihydro-1-ethyl-5-propyl-3-(3-trifluoromethylphenyl)-4(1H)-pyridinone
2,3-dihydro-3-ethylthio-1-propyl-5-(3-propylphenyl)-4(1H)-pyridinone
1-allyl-2,3-dihydro-5-(4-ethylphenyl)-3-(3-isopropoxyphenyl)-4(1H)-pyridinone
2,3-dihydro-5-(3-ethoxyphenyl)-3-(3-isopropylphenyl)-1-vinyl-4(1H)-pyridinone
3-(3-bromophenyl)-2,3-dihydro-5-isopropylthio-1-propyl-4(1H)-pyridinone
3-(2-bromophenyl)-2,3-dihydro-5-(3-ethoxyphenyl)-1-propargyl-4(1H)-pyridinone
2,3-dihydro-1-methyl-3,5-bis(3-trifluoromethylphenyl)-4(1H)-pyridinone
1-propyl-3-phenyl-5-(3-trifluoromethylphenyl)-4-piperidinone
3-(4-chlorophenyl)-1-ethyl-5-(3-fluorophenyl)-4-piperidinone
3-(3-fluorophenyl)-5-(2-fluorophenyl)-1-methyl-4-piperidinone
3-(3-bromophenyl)-1-ethyl-5-phenyl-4-piperidinone
3-(3-fluorophenyl)-1-methyl-5-phenoxy-4-piperidinone
3-(3-bromophenyl)-1-ethyl-5-phenylthio-4-piperidinone
3-methoxy-1-methyl-5-(3-trifluoromethylphenyl)-4-piperidinone
3-(3-bromophenyl)-1-methyl-5-propylthio-4-piperidinone
1-ethyl-3-(3-fluorophenyl)-4-piperidinone
3-(2-chlorophenyl)-5-(3-fluorophenyl)-1-methyl-4-piperidinone
3-(3-bromophenyl)-1-ethyl-5-propyl-4-piperidinone
3-(3-fluorophenyl)-5-methoxy-1-methyl-4-piperidinone
3-(3-bromophenyl)-1-methyl-4-piperidinone
3-(3-bromophenyl)-5-ethoxy-1-methyl-4-piperidinone
3-(3-fluorophenyl)-5-isopropylthio-1-methyl-4-piperidinone
3-(3-bromophenyl)-1,5-diethyl-4-piperidinone
3-ethylthio-1-methyl-5-(3-trifluoromethylphenyl)-4-piperidinone
3-(3-fluorophenyl)-1-methyl-5-methylthio-4-piperidinone
3-(3-fluorophenyl)-1-methyl-5-propoxy-4-piperidinone
3-(3-fluorophenyl)-5-isopropoxy-1-methyl-4-piperidinone
3-(3-chlorophenyl)-1-ethyl-5-(3-fluorophenyl)-4-piperidinone
3-(3-fluorophenyl)-1-methyl-5-(3-trifluoromethylphenyl)-4-piperidinone
3-(3-bromophenyl)-1-ethyl-5-isopropyl-4-piperidinone
3-(3-fluorophenyl)-1,5-dimethyl-4-piperidinone
1,3-dimethyl-5-(3-trifluoromethylphenyl)-4-piperidinone
3-(3-chlorophenyl)-5-(3-fluorophenyl)-1-methyl-4-piperidinone
3-isopropyl-1-methyl-5-(3-trifluoromethylphenyl)-4-piperidinone
1-ethyl-3-(4-fluorophenyl)-5-(3-trifluoromethylphenyl)-4-piperidinone
3-(3-chlorophenyl)-5-(2-methylphenyl)-1-propyl-4-piperidinone
3-(3-methoxyphenyl)-1-vinyl-4-piperidinone 3-(3-ethylphenyl)-1-isopropyl-5-(4-propylphenyl)-4-piperidinone
1-allyl-3-phenoxy-5-(3-propylphenyl)-4-piperidinone
1-ethyl-3-(3-methoxyphenyl)-5-(31-methylphenyl)-4-piperidinone
3-(3-isopropoxyphenyl)-5-methylthio-1-propargyl4-piperidinone
3-(4-bromophenyl)-5-(3-ethoxyphenyl)-1-(1-propenyl)-4-piperidinone
3-(2-ethylphenyl)-5-(3-propoxyphenyl)-1-vinyl-4-piperidinone
3-ethoxy-5-(3-methylphenyl)-1-propargyl-4-piperidinone
3-isopropyl-5-(3-isopropylphenyl)-1-(1-propenyl)-4-piperidinone
3-(3-chlorophenyl)-5-phenylthio-1-(1-propenyl)-4-piperidinone
1-isopropenyl-3-methyl-5-(3-propylphenyl)-4-piperidinone
1-isopropyl-3-(3-isopropylphenyl)-5-phenyl-4-piperidinone
3-(3-methoxyphenyl)-1-propyl-5-(2-trifluoromethylphenyl)-4-piperidinone
3-ethylthio-1-ethyl-5-(3-propoxyphenyl)-4-piperidinone
1-allyl-3-(3-ethylphenyl)-5-propoxy-4-piperidinone
3-(3-isopropoxyphenyl)-1-(1-propenyl)-4-piperidinone
3-(4-ethoxyphenyl)-5-(3-ethoxyphenyl)-1-isopropenyl-4-piperidinone
1-allyl-3-(3-methoxyphenyl)-5-propylthio-4-piperidinone
3-(3-chlorophenyl)-1-methyl-5-(2-propoxyphenyl)-4-piperidinone
3-(3-ethylphenyl)-1-vinyl-4-piperidinone
3-(3-isopropoxyphenyl)-5-phenoxy-1-propyl-4-piperidinone
3-(3-isopropoxyphenyl)-5-(3-propylphenyl)-1-propargyl-4-piperidinone
1-isopropenyl-31-(3-isopropylphenyl)-5-phenyl-4-piperidinone
3-ethyl-1-(1-propenyl)-5-(3-methylphenyl)-4-piperidinone
2,3-dihydro-3-(3-ethylphenyl)-1-ethyl-4(1H)-pyridinone
2,3-dihydro-3-ethyl-5-(3-isopropoxyphenyl)-1-(1-propenyl)-4(1H)-pyridinone
2,3-dihydro-1-methyl-5-(3-methylphenyl)-3-(4-propoxyphenyl)-4(1H)-pyridinone
5-(3-bromophenyl)-2,3-dihydro-1-isopropyl-3-(2-isopropylphenyl)-4(1H)-pyridinone
2,3-dihydro-5-(3-fluorophenyl)-1-vinyl-4(1)-pyridinone
2,3-dihydro-3-(3-ethylphenyl)-5-(3-methoxyphenyl)-1-vinyl-4(1H)-pyridinone
2,3-dihydro-3-(4-isopropoxyphenyl)-5-(3-trifluoromethylphenyl)-1-propargyl-4(1H)-pyridinone
2,3-dihydro-1-isopropenyl-5-isopropyl-3-(3-isopropylphenyl)-4(1H)-pyridinone
2,3-dihydro-1-ethyl-3-(4-trifluoromethylphenyl)-5-(3-trifluoromethylphenyl)-4(1H)-pyridinone
2,3-dihydro-3-ethyl-5-(3-methylphenyl)-1-(1-propenyl)-4(1H)-pyridinone
1-allyl-2,3-dihydro-5-(3-propylphenyl)-4(1H))-pyridinone
3-(3-chlorophenyl)-2,3-dihydro-5-(2-ethoxyphenyl)-1-vinyl-4(1H)-pyridinone
2,3-dihydro-5-(3-methoxyphenyl)-3-phenylthio-1-propargyl-4(1H)-pyridinone
2,3-dihydro-3-phenoxy-5-phenyl-1-(1-propenyl)-4(1H)-pyridinone
2,3-dihydro-5-phenyl-3-(3-trifluoromethylphenyl)-1-vinyl-4(1H)-pyridinone
3-butoxy-1-methyl-5-(3-trifluoromethylphenyl)-4-piperidinone
3-butylthio-1-ethyl-5-(3-fluorophenyl)-4-piperidinone
3-(t-butyl)-1-ethyl-5-(3-trifluoromethylphenyl)-4-piperidinone
3-(3-bromophenyl)-5-isobutyl-1-propyl-4-piperidinone
2,3-dihydro-3-isobutoxy-1-isopropyl-5-(3-methylphenyl)-4(1H)-pyridinone
5-butyl-2,3-dihydro-1-isopropyl-3-(3-propoxyphenyl)-4(1H)-pyridinone
3-(3-ethoxyphenyl)-5-isobutylthio-1-vinyl-4-piperidinone
2,3-dihydro-5-(3-ethylphenyl)-3-isobutylthio-1-propargyl-4-(1H)-pyridinone
1-allyl-3-(t-butoxy)-5-(3-chlorophenyl)-4-piperidinone
5-(t-butylthio)-2,3-dihydro-1-propyl-3-(3-propylphenyl)-4(1H)-pyridinone
3-butyl-1-ethyl-5-(3-isopropylphenyl)-4-piperidinone
3-butoxy-2,3-dihydro-5-(3-chlorophenyl)-1-propargyl-4(1H)-pyridinone The compounds of this invention are made by various known processes. The piperidinones can be made, as taught by Settimj et al., Gazz. Chim. Ital. 96, 604-11 (1966), by the condensation of 1-ethoxycarbonyl-1,3-diphenyl-2-propanones with formaldehyde and primary amines to form the corresponding piperidinones. This process, of course, is not usable to form the dihydropyridinones.

The piperidinones, particularly the 3,5-diphenyl-piperidinones, may be made from correspondingly substituted bispidinones. The reaction was explained by Gottarelli, Tetrahedron Letters, 2813–16 (1965), who showed the preparation of piperidinones from bispidinones by simple reaction with alkali or with sodium sulfide.

Both the piperidinones and dihydropyridinones are best made by the reduction of the corresponding 4(1H)-pyridinones with lithium aluminum hydride. The reduction was described in general by Tamura et al., Chem. Ind. (London), 168–69 (1972).

The pyridinone starting compounds are prepared by processes which are, in general, presently known in the art.

Benary and Bitter, Ber. 61, 1058 (1928) taught the synthesis of an intermediate disodium salt of 1,5-dihydroxy-2,4-diphenyl-1,4-pentadien-3-one by the condensation of 1,3-diphenyl-2-propanone with ethyl formate in the presence of sodium methoxide. The intermediate pentadienone is neutralized with strong acid to form 3,5-diphenyl-4-pyrone. Reaction of the pyrone with ammonium acetate at an elevated temperature produces 3,5-diphenyl-4(1H)-pyridinone.

Alternatively, 3,5-diphenyl-4(1H)-pyridinones can be prepared by the reaction of an appropriately ring-substituted 1,3-diphenyl-2-propanone with formamide and formamidine acetate. Reaction at reflux temperature produces the corresponding 3,5-diphenyl-4(1H)-pyridinone, which is reacted with a halide of the desired 1-substituent in the presence of a suitable strong base to form the desired starting compound.

The preferred synthesis of the pyridinones is adapted from the methods of Benary and Bitter and of El-Kholy et al., J. Hetero, Chem. 10, 665–67 (1973). An appropriately substituted 1-phenyl-2-propanone is formylated at low temperature with sodium methoxide and ethyl formate in ether, and the product is treated with an amine salt of the desired 1-substituent in aqueous medium. The resulting intermediate is predominantly a 1-amino-2-phenyl-1-buten-3-one. Some pyridinone is also formed at this step, as reported by El-Kholy et al. The butenone is reformylated as before, and spontaneously cyclizes to form the 1-substituted-3-phenyl-4(1H)-pyridinone.

The starting 2-propanones may be prepared by syntheses in the literature. For example, see Coan et al., J. Am. Chem. Soc. 76, 501 (1954); Sullivan et al., "Disodium Tetracarbonylferrate," American Laboratory 49–56 (June 1974); Collman et al., "Synthesis of Hemifluorinated Ketones using Disodium Tetracarbonylferrate," J. Am. Chem. Soc. 95, 2689–91 (1973); Collman et al., "Acyl and Alkyl Tetracarbonylferrate Complexes as Intermediates in the Synthesis of Aldehydes and Ketones," J. Am. Chem. Soc. 94, 2516–18 (1972).

The general synthesis methods of the pyridinones proceed from either ketone starting compounds or from carbonyl halides. The general process is the same, whichever starting compound is used. The general process will be discussed first, and reagents and reaction conditions will then be explained in detail.

The synthesis proceeds through an intermediate of the formula

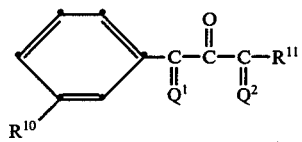

wherein
$Q^1$ and $Q^2$ independently represent 2 hydrogen atoms,
= CHOH, or an alkali metal salt thereof,
= $CHN(R^9)_2$ or
= $CHNHR^{12}$, provided that only one of $Q^1$ and $Q^2$ represents = $CHNHR^{12}$,
$R^{10}$ represents a $R^2$, $R^5$ or $R^8$ group,
$R^{11}$ represents a $R^1$, $R^4$ or $R^7$ group,
$R^{12}$ represents a R, $R^3$ or $R^6$ group.

The $R^9$ groups independently represent $C_1$-$C_3$ alkyl, or the $R^9$ groups combine with the nitrogen atom to which they are attached to form pyrrolidino, piperidino, morpholino, N-methylpiperazino and the like.

The =CHOH groups, which may be in the form of alkali metal salts, are provided by reaction with formylating agents which will be defined below. The =$CHN(R^9)_2$ groups are provided by reaction with aminoformylating agents, and the =$CHNHR^{12}$ groups are provided by exchanging either =CHOH groups or =$CHN(R^9)_2$ groups with amines of the formula $R^{12}NH_2$.

The intermediates described above are prepared from either ketones or carbonyl halides, as will be explained below. When $Q^1$ and $Q^2$ each represent 2 hydrogen atoms, the pyridinones are prepared by either 1. reacting with a formylating or aminoformylating agent;
2. reacting again with a formylating or aminoformylating agent; and
3. reacting with an amine of the formula $R^{12}NH_2$; or 1. reacting with a formylating or aminoformylating agent;
2. reacting with an amine of the formula $R^{12}NH_2$; and
3. reacting again with a formylating or aminoformylating agent.

When one of $Q^1$ and $Q^2$ represents either =CHOH or =$CHN(R^9)_2$, and the other represents 2 hydrogen atoms, the pyridinones are prepared by either 1. reacting with a formylating or aminoformylating agent; and
2. reacting with an amine of the formula $R^{12}NH_2$; or
1. reacting with an amine of the formula $R^{12}NH_2$; and
2. reacting with a formylating or aminoformylating agent.

When each of $Q^1$ and $Q^2$ represent either =CHOH or =$CHN(R^9)_2$, the pyridinones are prepared by reacting with an amine of the formula $R^{12}NH_2$.

The variations of the synthesis, and the preparation of the intermediates, will be sketched below.

When the process starts with a ketone of the general formula

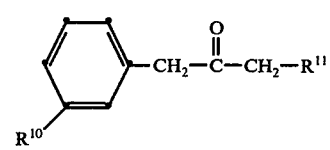

the first step is the formylation or aminoformylation of one of the methylene groups. If a formylating agent is used, a ketone of the formula

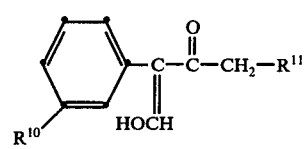

is produced. Reaction with an aminoformylating agent produces an enaminoketone such as (C) below.

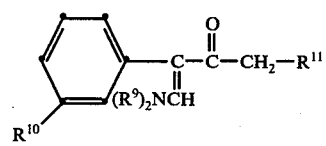

Organic chemists will understand that, although the sketches above show the first formylation or aminoformylation as occurring on a certain side of the ketone, it may in fact occur on either side of the ketone, depending on the activating characteristics of $R^{10}$ and $R^{11}$. The course of the reaction is the same in either case. It will also be understood that, in many instances, the product of the formylation or aminoformylation step will actually be a mixture containing the two possible monosubstituted compounds and the disubstituted compound.

The monosubstituted product is formylated or aminoformylated again, and exchanged with an amine of the formula $R^{12}NH_2$. The steps may be performed in either order. If the exchange is performed first, the intermediate product is an enaminoketone of the formula

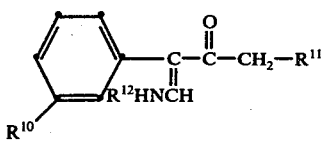

D.

Either formylation or aminoformylation of the above enaminoketone affords the pyridinone product, as the intermediate cyclizes as soon as the second group is introduced on the other methylene group.

Alternatively, either of compounds (B) or (C) may be either formylated or aminoformylated to provide intermediates of any of the formulae below.

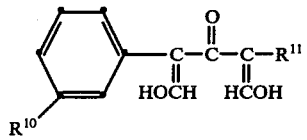

E.

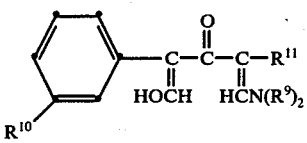

F.

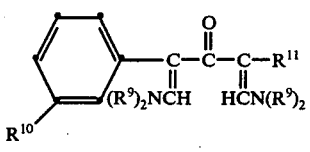

G.

It will be understood that the compound similar to (F), wherein the formyl and aminoformyl groups are reversed, is equivalent in all respects to compound (F). Pyridinones are formed from any of the above three intermediates by simple contact of the intermediate with an amine of the formula $R^{12}NH_2$.

When the starting compound is a carbonyl halide, the process proceeds essentially as described above, except for a first step performed as follows:

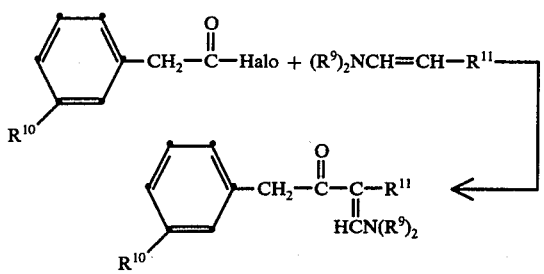

H.

It will be understood that reaction (H) can also be performed in the opposite manner, as shown below:

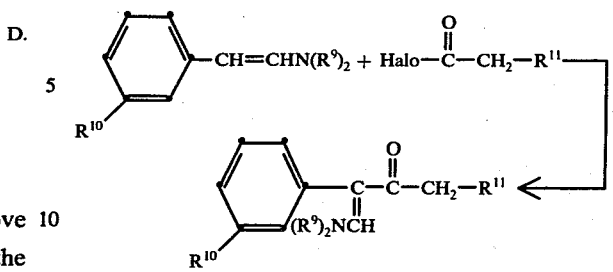

I.

It is also possible to form intermediates using phosgene as the carbonyl halide when the 3- and 5-substituents of the pyridinone are identical.

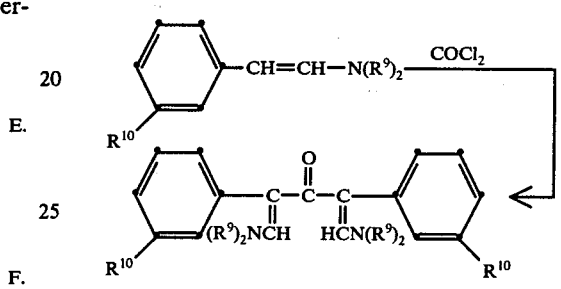

J.

The enaminoketones formed in equations (H), (I) and (J) above are identical to the intermediates described in (C) and (G) above, and are converted to the pyridinones as described above.

Alternatively, it is possible to prepare the 1-unsubstituted pyridinones by using $NH_3$ in place of $R^{12}NH_2$ in the process, or by using the process of Benary and Bitter. The pyridinone is then alkylated at the 1-position with a halide of $R^{12}$ according to common procedures.

As a chemist would expect, the amines, $R^{12}NH_2$, may be used in the form of salts, preferably hydrohalide salts, including hydrochlorides, hydrobromides and the like. Such salts are often more convenient than the free amines.

The formylating agents used in the process are chosen from the common agents used for such reactions. The preferred agents are esters of formic acid of the formulae

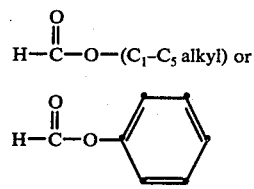

Similar formylations are discussed in Organic Syntheses 300–02, Collective Vol. III (1955).

The esters are used in the presence of strong bases, of which alkali metal alkoxides are preferred, such as sodium methoxide, potassium ethoxide and lithium propoxide. Other bases may also be used, including alkali metal hydrides, alkali metal amides, and inorganic bases including alkali metal carbonates and hydroxides. Such strong organic bases as diazabicyclononane and diazabicycloundecane are also useful.

Reactions with formylating agents are performed in aprotic solvents such as are regularly used in chemical synthesis. Ethyl ether is usually the preferred solvent. Ethers in general, including solvents such as ethyl propyl ether, ethyl butyl ether, 1,2-dimethoxyethane and tetrahydrofuran, aromatic solvents such as benzene and xylene, and alkanes such as hexane and octane can be used as formylation solvents.

Because of the strong bases used in the formylation reactions, low temperatures produce the best yields. Reaction at temperatures in the range of from about −25° C. to about 10° C. is preferred. The reaction mixture may be allowed to warm to room temperature, however, after the reaction has proceeded part way to completion. Reaction times from about 1 to about 24 hours are adequate for economic yields in the formylation reactions.

The aminoformylating agents used in these syntheses may be any compounds capable of reacting with an active methylene group to introduce a $=CHN(R^9)_2$ group, or its acid addition salt. Such agents are chosen from among s-triazine, the orthoformamides,

the formate ester animals,

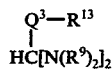

the formamide acetals

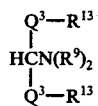

the tris(formylamino)methanes,

and the formiminium halides,

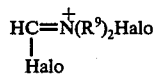

$Q^3$ in the structures above represents oxygen or sulfur, and $R^{13}$ represents $C_1-C_6$ alkyl or phenyl.

Useful references on the aminoformylating agents include DeWolfe, Carboxylic Acid Derivatives 420–506 (Academic Press 1970), and Ulrich, Chemistry of Imidoyl Halides 87–96 (Plenum Press 1968). Bredereck et al. have written many papers on such agents and reactions, of which the following are typical. Ber. 101, 4048–56 (1968); Ber. 104, 2709–26 (1971); Ber. 106, 3732–42 (1973); Ber. 97, 3397–406 (1964); Ann. 762, 62–72 (1972); Ber. 97, 3407–17 (1964); Ber. 103, 210–21 (1970); Angew. Chem. 78, 147 (1966); Ber. 98, 2887–97 (1965); Ber. 96, 1505–14 (1963); Ber. 104, 3475–85 (1971); Ber. 101, 41–50 (1968); Ber. 106, 3725–31 (1973); and Angew. Chem. Int'l. Ed. 5, 132 (1966). Other notable papers on the subject include Kreutzberger et al., Arch. der Pharm. 301, 881–96 (1968), and 302, 362–75 (1969), and Weingarten et al., J. Org. Chem. 32, 3293–94 (1967).

Aminoformylations are usually carried out without solvent, at elevated temperatures from about 50° C. to about 200° C. Solvents such as dimethylformamide are sometimes used, however, particularly when it is desirable to raise the boiling point of the reaction mixture.

The exchange reactions with $R^{12}NH_2$ are best performed in protic solvents of which alkanols are preferred and ethanol is most appropriate. Temperatures from about −20° C. to about 100° C. can be used for the exchange reactions. Room temperature is satisfactory and is preferred.

In general, intermediate compounds in the synthesis are not purified, but are simply used in successive steps after separation by extraction, neutralization or removal of excess solvent or reactant as appropriate.

The enamine acylation reactions, H-J, are performed in the presence of bases such as tertiary amines, alkali metal carbonates, magnesium oxide and the like, and in aprotic solvents as described above.

In some instances, as organic chemists will understand, it is necessary to apply additional synthetic steps after the pyridinone has been formed. For example, it is convenient to form compounds having an alkoxy $R^5$ or $R^8$ substituent by first making the corresponding hydroxy-substituted compound, and then substituting on the oxygen atom.

The compounds of the present invention are most efficiently formed from the corresponding 4(1H)-pyridinones by reduction with lithium aluminum hydride. The reaction is carried out by simple contact of the starting compound with the reducing agent in a solvent. The reaction may be performed at room temperature, or it may be accelerated by heating the reaction mixture moderately. In general, temperatures from about 0° C. to about 50° C. can be used.

Solvents for the reaction may be any of the typical inert organic reaction solvents, of which diethyl ether is preferred. Other ethers, including tetrahydrofuran, isopropyl ether and the like, alkanes including hexane and octane, and aromatics such as benzene and xylene, are also usable solvents.

As one would of course expect, reduction of the pyridinones produces a mixture of products. First one, and then the other, of the two double bonds in the pyridinone ring are reduced by the reaction. Necessarily, the reaction produces a porportion of the 2,3-dihydropyridinone, a proportion of the 5,6-dihydropyridinone, and a proportion of the piperidinone. The products are readily separated according to the usual methods. Column chromatography is usually the preferred method of separation.

It is believed that the above description of the synthesis is adequate to enable an organic chemist to prepare any compound of this invention. The following specific examples are provided merely as assistance to the chemist, to assure that all of the compounds are accessible.

In the examples below, the products were identified by elemental microanalysis, thin-layer chromatography, nuclear magnetic resonance analysis, infrared analysis, ultraviolet analysis, and mass spectroscopy as was required or convenient in each case.

All temperatures in the examples below are on the Celsius scale.

EXAMPLE 1

2,3-dihydro-1-methyl-3-phenyl-5-(3-trifluoromethylphenyl)-4(1H)-pyridinone

EXAMPLE 2

2,3-dihydro-1-methyl-5-phenyl-3-(3-trifluoromethylphenyl)-4(1H)-pyridinone

EXAMPLE 3

1-methyl-3-phenyl-5-(3-trifluoromethylphenyl)-4-piperidinone

A 556 g. portion of 1-phenyl-3-(3-trifluoromethylphenyl)-2-propanone was added to 4000 ml. of tetrahydrofuran containing 284 g. of sodium methoxide at 10°-15°. The addition was carried out over a 20 minute period with constant stirring while the temperature was held below 15°, and the mixture was then stirred for 15 minutes more. Then 370 g. of ethyl formate was added over a 30 minute period, and the complete mixture was stirred 1 hour more at 10°-15°. A second portion of 296 g. of ethyl formate was then added slowly and the mixture was stirred overnight while it was allowed to warm to room temperature.

A solution of 336 g. of methylamine hydrochloride in 1300 ml. of water was then added, and the mixture was stirred for ½ hour more. The phases were then allowed to separate, and the organic layer was concentrated under vacuum. The residue was dissolved in methylene chloride, dried over sodium sulfate and concentrated to an oil, which weighed 723 g.

The oil was added to 4000 ml. of tetrahydrofuran, 284 g. of sodium methoxide was added, and the process described above was repeated, using the same weights of ethyl formate and of methylamine hydrochloride. The oily residue obtained from evaporation of the reaction mixture was dissolved in methylene chloride, washed with water and dried over sodium sulfate. The methylene chloride was evaporated under vacuum, and the residue crystallized upon standing. A small amount of diethyl ether was added to form a thick slurry which was chilled overnight. Filtration of the chilled slurry produced 430 g. of 1-methyl-3-phenyl-5-(3-trifluoromethylphenyl)-4(1H)-pyridinone, m.p. 153°.

A 21 g. portion of the above intermediate was dissolved in 500 ml. of diethyl ether and 5 g. of lithium aluminum hydride was added. The mixture was stirred at reflux temperature for 3 hours, and excess hydride was decomposed by adding successively 5 ml. of water, 15 ml. of 15 percent sodium hydroxide solution and 5 ml. more of water. The reaction mixture was then cooled and stirred overnight, and filtered through anhydrous magnesium sulfate. The filtrate was concentrated under vacuum to produce an oil which was separated by chromatography over a silica gel column.

The various fractions were eluted with benzene-ethyl acetate mixtures. The 5th and 6th fractions obtained contained primarily the two dihydro compounds, which were separated by additional stages of chromatography to obtain about 4.3 g. of the compounds of Examples 1 and 2. The compounds were identified by nuclear magnetic resonance analysis and by mass spectroscopy, which indicated a molecular weight of 331 for each.

About 4.1 g. of the compound of Example 3, m.p. 86.5°-87.5°, was obtained from the 7th, 8th and 9th fractions.

|   | Theoretical | Found |
|---|---|---|
| C | 68.46% | 68.19% |
| H | 5.44 | 5.49 |
| N | 4.20 | 4.37 |

EXAMPLE 4

2,3-dihydro-1-methyl-3-(3-methylphenyl)-5-phenyl-4(1H)-pyridinone

EXAMPLE 5

2,3-dihydro-1-methyl-5-(3-methylphenyl)-3-phenyl-4(1H)-pyridinone

EXAMPLE 6

1-methyl-3-(3-methylphenyl)-5-phenyl-4-piperidinone

A 22.8 g. portion of 1-(3-methylphenyl)-3-phenyl-2-propanone was reacted with ethyl formate and methylamine hydrochloride as described in Examples 1-3 to produce 7 g. of 1-methyl-3-(3-methylphenyl)-5-phenyl-4(1H)-pyridinone.

The above intermediate pyridinone was reduced with 2 g. of lithium aluminum hydride in 100 ml. of diethyl ether as described in Examples 1-3.

The second fraction obtained by column chromatography on silica gel with benzene-ethyl acetate was the piperidinone of Example 6, m.p. 100°-103°, yield 1.5 g.

|   | Theoretical | Found |
|---|---|---|
| C | 81.10% | 80.98% |
| H | 8.24 | 8.00 |
| N | 4.98 | 4.87 |

The first fractions off the column contained the compounds of Examples 4 and 5, which were separated by further stages of chromatography with benzene-ethyl acetate. The yield of the compound of Example 4 was about 500 mg., and it was identified by nuclear magnetic resonance analysis and mass spectroscopy. About 750 mg. of the product of Example 5 was obtained. The product had a melting point of 72°-76° and the elemental microanalysis was as follows.

|   | Theoretical | Found |
|---|---|---|
| C | 82.28% | 82.23% |
| H | 6.90 | 7.00 |
| N | 5.05 | 4.83 |

EXAMPLE 7

3,5-bis(3-fluorophenyl)-1-methyl-4-piperidinone

A 10.5 g. portion of 1,3-bis(3-fluorophenyl)-2-propanone was mixed with 16.2 g. of formaldehyde and 8 g. of 40 percent aqueous methylamine solution in 75 ml. of denatured ethanol. The mixture was stirred at reflux temperature overnight, cooled and filtered. The recovered solids were identified as 13 g. of essentially pure 3,5-bis(3-fluorophenyl)-N,N-dimethylbispidinone.

A 7.1 g. portion of the bispidinone was combined with 2.8 g. of hydroxylamine hydrochloride and 3.3 g. of sodium methoxide in 50 ml. of 75 percent aqueous acetic acid. The mixture was stirred at reflux for 6 hours, cooled, and partially evaporated under vacuum to remove most of the acetic acid. The concentrated solution was poured into a large amount of water and extracted with chloroform. The organic extract was dried over magnesium sulfate and concentrated under vacuum. The residue was made basic with aqueous sodium hydroxide and extracted again with chloroform. Evaporation of the chloroform extract under vacuum produced 0.7 g. of 3,5-bis(3-fluorophenyl)-1-methyl-4-piperidinone, molecular weight 301 by mass spectroscopy.

EXAMPLE 8

2,3-dihydro-3-(4-fluorophenyl)-1-methyl-5-(3-trifluoromethylphenyl)-4(1H)-pyridinone

EXAMPLE 9

2,3-dihydro-5-(4-fluorophenyl)-1-methyl-3-(3-trifluoromethylphenyl)-4(1H)-pyridinone

EXAMPLE 10

3-(4-fluorophenyl)-1-methyl-5-(3-trifluoromethylphenyl)-4-piperidinone

A 28 g. portion of 1-(4-fluorophenyl)-3-(3-trifluoromethylphenyl)-2-propanone was reacted with ethyl formate and methylamine hydrochloride as described in Examples 1-3 to produce 10 g. of 3-(4-fluorophenyl)-1-methyl-5-(3-trifluoromethylphenyl)-4(1H)-pyridinone.

The above pyridinone was reduced with 2 g. of lithium aluminum hydride as described in Examples 1-3. The various products were separated by chromatography as described above to produce about 0.8 g. each of the three compounds named in the heading, which were identified as follows. Example 8, m.p. 89°-91°.

|   | Theoretical | Found |
|---|---|---|
| C | 65.33% | 65.06% |
| H | 4.33 | 4.24 |
| N | 4.01 | 3.89 |

Example 9, molecular weight 349 by mass spectroscopy. Example 10, m.p. 84°-85°.

|   | Theoretical | Found |
|---|---|---|
| C | 64.96% | 65.18% |
| H | 4.84 | 4.79 |
| N | 3.99 | 3.95 |

EXAMPLE 11

3,5-bis(3-chlorophenyl)-2,3-dihydro-1-methyl-4(1H)-pyridinone

EXAMPLE 12

3,5-bis(3-chlorophenyl)-1-methyl-4-piperidinone

A 10 g. portion of 1,3-bis(3-chlorophenyl)-2-propanone was reacted with ethyl formate and methylamine hydrochloride to produce 7 g. of 3,5-bis(3-chlorophenyl)-1-methyl-4(1H)-pyridinone. A 6.4 g. portion of the pyridinone was reduced with 2 g. of lithium aluminum hydride and the products were separated by chromatography as described in the examples above. The yields were about 0.8 g. of Example 11, and 1.5 g. of Example 12. Example 11, m.p. 140°.

|   | Theoretical | Found |
|---|---|---|
| C | 64.49% | 64.58% |
| H | 5.41 | 5.77 |
| N | 4.18 | 4.07 |

Example 12, m.p. 79°.

|   | Theoretical | Found |
|---|---|---|
| C | 64.68% | 64.94% |
| H | 5.13 | 5.25 |
| N | 4.19 | 4.24 |

EXAMPLE 13

5-(3-bromophenyl)-2,3-dihydro-1-methyl-3-phenyl-4(1H)-pyridinone

EXAMPLE 13a 3-(3-bromophenyl)-2,3-dihydro-1-methyl-5-phenyl-4(1H)-pyridinone

EXAMPLE 14

3-(3-bromophenyl)-1-methyl-5-phenyl-4-piperidinone

A 10 g. portion of 3-(3-bromophenyl)-1-methyl-5-phenyl-4(1H)-pyridinone was made from 22 g. of the corresponding 2-propanone as described in Examples 1-3. The pyridinone was reduced with 2 g. of lithium aluminum hydride as described in the examples above, and the reaction mixture was chromatographed as described above with benzene-ethyl acetate mixtures. The combined yield of the compounds of Examples 13 and 13a was 4 g., molecular weight 341 by mass spectroscopy. The yield of the compound of Example 14 was 0.5 g., molecular weight by mass spectroscopy 343.

EXAMPLE 15

5-(3-chlorophenyl)-3-(4-chlorophenyl)-2,3-dihydro-1-methyl-4(1H)-pyridinone

EXAMPLE 16

3-(3-chlorophenyl)-5-(4-chlorophenyl)-2,3-dihydro-1-methyl-4(1H)-pyridinone

EXAMPLE 17

3-(3-chlorophenyl)-5-(4-chlorophenyl)-1-methyl-4-piperidinone

A 10 g. portion of 3-(3-chlorophenyl)-5-(4-chlorophenyl)-1-methyl-4(1H)-pyridinone was made from 33.6 g. of the corresponding 2-propanone by the procedures of Examples 1-3. The pyridinone was reduced with lithium aluminum hydride and the reaction mixture was separated by chromatography as described in the examples above. The products of Examples 15 and 16 were obtained as a mixture containing both, combined yield 2.1 g., m.p. 125.5°.

|   | Theoretical | Found |
|---|---|---|
| C | 65.00% | 65.15% |
| H | 4.55 | 4.65 |
| N | 4.22 | 4.31 |

The compound of Example 17 was obtained in a yield of 1.8 g., m.p. 118.5°-126.5°.

|   | Theoretical | Found |
|---|---|---|
| C | 64.68% | 64.45% |

|   | Theoretical | Found |
|---|---|---|
| H | 5.13 | 4.93 |
| N | 4.19 | 4.32 |

EXAMPLE 18

5-(4-chlorophenyl)-2,3-dihydro-1-methyl-3-(3-trifluoromethylphenyl)-4(1H)-pyridinone

EXAMPLE 19

3-(4-chlorophenyl)-2,3-dihydro-1-methyl-5-(3-trifluoromethylphenyl)-4(1H)-pyridinone

EXAMPLE 20

3-(4-chlorophenyl)-1-methyl-5-(3-trifluoromethylphenyl)-4-piperidinone

A 15 g. portion of 1-(4-chlorophenyl)-3-(3-trifluoromethylphenyl)-2-propanone was reacted with ethyl formate and methylamine hydrochloride to prepare 10 g. of 3-(4-chlorophenyl)-1-methyl-5-(3-trifluoromethylphenyl)-4(1H)-pyridinone. The intermediate pyridinone was reduced with lithium aluminum hydride. Column chromatographic separation of the reaction mixture on a silica gel column as described in the examples above produced about 0.5 g. of the compound of Example 18, m.p. 122.5°, about 1.1 g. of the compound of Example 19, m.p. 113.5°, and about 1.3 g. of the compound of Example 20, m.p. 115.5°.

|   | Example 18 | |
|---|---|---|
|   | Theoretical | Found |
| C | 62.39% | 62.68% |
| H | 4.13 | 4.10 |
| N | 3.83 | 3.75 |
|   | Example 19 | |
|   | Theoretical | Found |
| C | 62.39% | 62.11% |
| H | 4.13 | 4.36 |
| N | 3.83 | 3.83 |
|   | Example 20 | |
|   | Theoretical | Found |
| C | 62.05% | 61.75% |
| H | 4.66 | 4.74 |
| N | 3.81 | 3.86 |

EXAMPLE 21

3-(2-chlorophenyl)-2,3-dihydro-1-methyl-5-(3-trifluoromethylphenyl)-4(1H)-pyridinone

EXAMPLE 22

5-(2-chlorophenyl)-2,3-dihydro-1-methyl-3-(3-trifluoromethylphenyl)-4(1H)-pyridinone

EXAMPLE 23

3-(2-chlorophenyl)-1-methyl-5-(3-trifluoromethylphenyl)-4-piperidinone

Ten g. of 3-(2-chlorophenyl)-1-methyl-5-(3-trifluoromethylphenyl)-4(1H)-pyridinone was prepared from 35 g. of 1-(2-chlorophenyl)-3-(3-trifluoromethylphenyl)-2-propanone by reaction with ethyl formate and methylamine hydrochloride as described in Examples 1-3. The pyridinone was reduced with 2 g. of lithium aluminum hydride and excess hydride was decomposed and the product worked up and chromatographed as described in Examples 1-3. The recovered yields were about 1.3 g. of a mixture of the compounds of Examples 21 and 22, which were identified by mass spectroscopy with an indicated molecular weight of 365. About 2.1 g. of the compound of Example 23 was recovered, m.p. 90°-92°. The elemental analysis of Example 23 was as follows.

|   | Theoretical | Found |
|---|---|---|
| C | 62.05% | 62.06% |
| H | 4.66 | 4.68 |
| N | 3.81 | 3.74 |

EXAMPLE 24

2,3-dihydro-3-(3-methoxyphenyl)-1-methyl-5-phenyl-4(1H)-pyridinone

EXAMPLE 25

2,3-dihydro-5-(3-methoxyphenyl)-1-methyl-3-phenyl-4(1H)-pyridinone

EXAMPLE 26

3-(3-methoxyphenyl)-1-methyl-5-phenyl-4-piperidinone

A 54 g. portion of 1-(3-methoxyphenyl)-3-phenyl-2-propanone was reacted with ethyl formate and methylamine hydrochloride as described in Examples 1-3 to prepare 10 g. of 3-(3-methoxyphenyl)-1-methyl-5-phenyl-4(1H)-pyridinone, which was reduced with 2 g. of lithium aluminum hydride. The reaction mixture was worked up as in the examples above and chromatographed over a silica gel column. About 1.4 g. of a mixture of the compounds of Examples 24 and 25 was obtained, an oil which was identified by mass spectroscopy as having a molecular weight of 293. About 1.3 g. of the piperidinone of Example 26 was recovered, which had an indicated molecular weight of 295 by mass spectroscopy.

EXAMPLE 27

2,3-dihydro-1-ethyl-3-phenyl-5-(3-trifluoromethylphenyl)-4(1H)-pyridinone

EXAMPLE 28

2,3-dihydro-1-ethyl-5-phenyl-3-(3-trifluoromethylphenyl)-4(1H)-pyridinone

EXAMPLE 29

1-ethyl-3-phenyl-5-(3-trifluoromethylphenyl)-4-piperidinone

An 11.5 g. portion of 1-phenyl-3-(3-trifluoromethylphenyl)-2-propanone was reacted with ethyl formate and ethylamine hydrochloride as described in Examples 1-3 to produce 6.8 g. of 1-ethyl-3-phenyl-5-(3-trifluoromethylphenyl)-4(1H)-pyridinone, which was reduced with 2 g. of lithium aluminum hydride as described above. After column chromatography as described in the examples above, the products of Examples 27 and 28 were recovered as a mixture. Mass spectroscopy of the mixture showed a molecular weight of 345, and the yield was 1.2 g. The molecular weight of the product of Example 29 was indicated as 347 by mass spectroscopy, yield 1.9 g.

EXAMPLE 30

2,3-dihydro-5-ethyl-1-methyl-3-(3-trifluoromethylphenyl)-4(1H)-pyridinone

EXAMPLE 31

2,3-dihydro-3-ethyl-1-methyl-5-(3-trifluoromethylphenyl)-4(1H)-pyridinone

EXAMPLE 32

3-ethyl-1-methyl-5-(3-trifluoromethylphenyl)-4-piperidinone

Seventy g. of 1-piperidino-1-butene and 77 g. of triethylamine were dissolved in 1500 ml. of diethyl ether at 0°. A 112 g. portion of 3-trifluoromethylphenylacetyl chloride dissolved in 700 ml. of diethyl ether was added dropwise, and the mixture was stirred for 2 hours at 0° after completion of the addition. The mixture was then evaporated to dryness under vacuum, and the residue was taken up in methylene chloride. The solution was washed with water, dried and evaporated to an oily residue.

The above residue was combined with 500 ml. of dimethylformamide dimethyl acetal and heated at reflux temperature for 12 hours. The mixture was then evaporated under vacuum, and the residue was mixed with 700 ml. of denatured ethanol and 150 g. of methylamine hydrochloride. The ethanol solution was heated at reflux for 12 hours more and evaporated to dryness. The residue was taken up in methylene chloride, washed with water, dried, and evaporated to dryness again. The residue was slurried in diethyl ether and filtered. Separation of the solids by column chromatography on silica gel produced 10.5 g. of 3-ethyl-1-methyl-5-(3-trifluoromethylphenyl)-4(1H)-pyridinone.

The pyridinone intermediate was reduced with 2 g. of lithium aluminum hydride and worked up and chromatographed as described in the examples above. The products of Examples 30 and 31 were isolated as a mixture, with a combined yield of 1.2 g. Mass spectroscopy of the product showed an indicated molecular weight of 283. The product of Example 32, 2.6 g., had a molecular weight of 285 by mass spectroscopy.

EXAMPLE 33

1-allyl-2,3-dihydro-5-phenyl-3-(3-trifluoromethylphenyl)-4(1H)-pyridinone

EXAMPLE 34

1-allyl-2,3-dihydro-3-phenyl-5-(3-trifluoromethylphenyl)-4(1H)-pyridinone

EXAMPLE 35

1-allyl-3-phenyl-5-(3-trifluoromethylphenyl)-4-piperidinone

Twenty g. of 1-phenyl-3-(3-trifluoromethylphenyl)-2-propanone was reacted with ethyl formate and allylamine hydrochloride as described in Examples 1-3 to obtain 10.8 g. of 1-allyl-3-phenyl-5-(3-trifluoromethylphenyl)-4(1H)-pyridinone, which was reacted with 2 g. of lithium aluminum hydride as described in Examples 1-3. The reaction mixture was worked up and chromatographed as described in the examples above to obtain 1.2 g. of the products of Examples 33 and 34 as a mixture. The compounds were identified by mass spectroscopy, which showed an indicated molecular weight of 357. A yield of 1.0 g. of the compound of Example 35 was obtained, which showed a mass spectroscopy molecular weight of 359.

EXAMPLE 36

2,3-dihydro-1-methyl-3-(3-trifluoromethylphenyl)-4(1H)-pyridinone

EXAMPLE 36a 2,3-dihydro-1-methyl-5-(3-trifluoromethylphenyl)-4(1H)-pyridinone

EXAMPLE 37

1-methyl-3-(3-trifluoromethylphenyl)-4-piperidinone

A mixture of 50 g. of 3-trifluoromethylphenyl acetone and 100 ml. of dimethylformamide dimethyl acetal in 200 ml. of dimethylformamide was stirred at reflux temperature for 5 days. The excess volatile ingredients were then removed under vacuum and the residual oil was taken up in 200 ml. of ethanol. One hundred g. of methylamine hydrochloride was added and the mixture was refluxed overnight. After cooling, precipitated amine was filtered off and the filtrate was evaporated under vacuum. The residual oil was taken up in methylene chloride and washed twice with 300 ml. portions of water and once with 400 ml. of saturated NaCl solution. The organic solution was then dried over magnesium sulfate and evaporated under vacuum to an oily residue which was taken up in 400 ml. of diethyl ether, cooled and filtered. The solids were recrystallized from isopropyl ether-methylene chloride to produce 10 g. of 1-methyl-3-(3-trifluoromethylphenyl)-4(1H)-pyridinone.

The above pyridinone was reduced with lithium aluminum hydride and the reaction mixture was worked up and chromatographed as described in the examples above. About 1.5 g. of the product of Example 36 was obtained, m.p. 64°-65° C.

|   | Theoretical | Found |
|---|---|---|
| C | 61.17% | 60.96% |
| H | 4.74 | 4.70 |
| N | 5.49 | 5.51 |

About 1.5 g. of the product of Example 37 was obtained, and was found to have an indicated molecular weight by mass spectroscopy of 257. The product of Example 36a was recovered in the amount of 0.15 g.

The compounds described above have been tested in a number of herbicidal test systems to determine the range of their herbicidal efficacy. The results produced by the compounds in the representative tests reported below are exemplary of the outstanding activity of the compounds.

Compound application rates are expressed in kilograms of the compound per hectare of land (kg./ha.) throughout this specification and claims.

Blank spaces in the tables below indicate that the compound was not tested against the named species. In some instances, the results of testing a compound repeatedly against a plant species have been averaged.

Untreated control plants or plots were included in all tests. Ratings of the control produced by the compounds were made by comparison of the treated plants or plots with the controls.

Test 1 broad spectrum greenhouse test

Square plastic pots were filled with a sterilized sandy loam soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the components were applied, the pots were moved to the greenhouse, watered as necessary, and observed and rated about 10–13 days after application of the compounds. Untreated control plants were used as standards in every test.

The table below reports results of testing typical compounds of the invention. The compounds are identified by their example numbers above.

Herbicidal effect was rated on a 1-5 scale, where 1 indicates normal plants, and 5 indicates death of the plants or no emergence.

Table 1

| Compound of Example No. | Preemergence | | | Postemergence | | |
|---|---|---|---|---|---|---|
| | Tomato | Crabgrass | Pigweed | Tomato | Crabgrass | Pigweed |
| 1 ⟍** | 5 | 5 | 5 | 4 | 4 | 4 |
| 2 ⟋ | | | | | | |
| 3 | 4 | 5 | 5 | 4 | 4 | 3 |
| 4 | 4 | 5 | 4 | 4 | 4 | 3 |
| 5* | 4 | 5 | 4 | 4 | 4 | 3 |
| 6 | 3 | 4 | 3 | 4 | 4 | 3 |
| 8 ⟍** | 5 | 5 | 5 | 3 | 4 | 3 |
| 9 ⟋ | | | | | | |
| 10 | 5 | 5 | 5 | 3 | 4 | 3 |
| 15 ⟍** | 4 | 5 | 5 | 3 | 2 | 3 |
| 16 ⟋ | | | | | | |
| 19 | 4 | 5 | 5 | 4 | 4 | 4 |
| 20 | 2 | 5 | 5 | 2 | 2 | 3 |
| 23 | 2 | 4 | 4 | 3 | 3 | 2 |
| 26 | 4 | 4 | 4 | 3 | 3 | 2 |
| 27 ⟍** | 4 | 5 | 5 | 3 | 3 | 2 |
| 28 ⟋ | | | | | | |
| 29 | 4 | 4 | 4 | 3 | 3 | 2 |

*Tested as a mixture containing a substantial amount of the compound of Ex. 4.
**Tested as a mixture.

Test 2 seven-species greenhouse test

The test was conducted in general like the test described in Test 1. In this test, the seeds were planted in flat metal trays, rather than in pots. The compounds were formulated according to the procedure above, except that about 6 g./100 ml. of the compound was dissolved in the surfactant-containing solvent, and about 1 part of the organic solution was diluted with 12 parts of water before application to the trays. The compounds were applied at the rate of 9.0 kg./ha., and the results of testing against the species named below were as follows.

Table 2

| Compound of Example No. | Preemergence | | | | | | | Postemergence | | | | | | |
|---|---|---|---|---|---|---|---|---|---|---|---|---|---|---|
| | Corn | Large Crabgrass | Pigweed | Foxtail | Velvetleaf | Morningglory | Zinnia | Corn | Large Crabgrass | Pigweed | Foxtail | Velvetleaf | Morningglory | Zinnia |
| 1 ⟍** | 5 | 5 | 5 | 5 | 5 | 5 | 5 | 4 | 4 | 3 | 3 | 3 | 3 | 3 |
| 2 ⟋ | | | | | | | | | | | | | | |
| 3 | 3 | 5 | 5 | 5 | 5 | 4 | 4 | 4 | 4 | 3 | 3 | 3 | 3 | 2 |
| 4 | 3 | 5 | 5 | 5 | 5 | 4 | 5 | 2 | 2 | 2 | 2 | 2 | 2 | 2 |
| 5* | 3 | 5 | 4 | 5 | 4 | 4 | 3 | 3 | 2 | 2 | 2 | 2 | 2 | 2 |
| 6 | 2 | 4 | 3 | 3 | 3 | 3 | 2 | 2 | 2 | 2 | 2 | 2 | 2 | 2 |
| 7 | 4 | 5 | 5 | 5 | 5 | 5 | 3 | 2 | 2 | 2 | 2 | 2 | 2 | 2 |
| 8 | 4 | 5 | 5 | 5 | 5 | 5 | 5 | 3 | 3 | 2 | 3 | 3 | 2 | 3 |
| 8 ⟍** | 4 | 5 | 5 | 5 | 5 | 5 | 5 | 3 | 2 | 2 | 2 | 2 | 2 | 2 |
| 9 ⟋ | | | | | | | | | | | | | | |
| 10 | 3 | 5 | 5 | 5 | 5 | 4 | 5 | 3 | 3 | 2 | 3 | 3 | 2 | 3 |
| 11 | 3 | 5 | 5 | 5 | 5 | 5 | 3 | 3 | 3 | 3 | 4 | 3 | 2 | 3 |
| 12 | 3 | 5 | 5 | 5 | 3 | 2 | 2 | 2 | 2 | 2 | 2 | 2 | 2 | 2 |
| 13 ⟍** | 4 | 5 | 5 | 5 | 5 | 4 | 4 | 3 | 3 | 2 | 2 | 2 | 2 | 2 |
| 13a ⟋ | | | | | | | | | | | | | | |
| 14 | 4 | 5 | 5 | 5 | 5 | 3 | 2 | 2 | 3 | 2 | 2 | 2 | 2 | 2 |
| 15 ⟍** | 3 | 5 | 3 | 4 | 5 | 3 | 2 | 2 | 2 | 2 | 2 | 2 | 2 | 2 |
| 16 ⟋ | | | | | | | | | | | | | | |
| 17 | 2 | 3 | 2 | 3 | 2 | 1 | 1 | 2 | 2 | 2 | 2 | 2 | 3 | 2 |
| 18 | 3 | 5 | 4 | 4 | 4 | 2 | 2 | 2 | 2 | 2 | 2 | 2 | 2 | 2 |

Table 2-continued

| Compound of Example No. | Preemergence | | | | | | | Postemergence | | | | | | |
|---|---|---|---|---|---|---|---|---|---|---|---|---|---|---|
| | Corn | Large Crab-grass | Pig-weed | Fox-tail | Velvet-leaf | Morning-glory | Zinnia | Corn | Large Crab-grass | Pig-weed | Fox-tail | Velvet-leaf | Morning-glory | Zinnia |
| 19 | 3 | 5 | 5 | 5 | 5 | 3 | 2 | 3 | 2 | 3 | 3 | 2 | 2 | 2 |
| 20 | 2 | 5 | 5 | 3 | 2 | 1 | 1 | 2 | 2 | 2 | 2 | 2 | 2 | 2 |
| 21 | 4 | 5 | 5 | 4 | 5 | 5 | 4 | 3 | 2 | 2 | 2 | 2 | 2 | 2 |
| 22** | | | | | | | | | | | | | | |
| 23 | 3 | 5 | 4 | 4 | 3 | 2 | 1 | 3 | 2 | 2 | 3 | 2 | 2 | 3 |
| 24 | 4 | 5 | 5 | 5 | 5 | 5 | 4 | 3 | 2 | 2 | 2 | 2 | 2 | 2 |
| 25** | | | | | | | | | | | | | | |
| 26 | 3 | 5 | 2 | 4 | 2 | 1 | 2 | 2 | 2 | 2 | 2 | 2 | 2 | 2 |
| 27 | 4 | 5 | 5 | 5 | 5 | 4 | 4 | 3 | 2 | 2 | 2 | 2 | 2 | 2 |
| 28** | | | | | | | | | | | | | | |
| 29 | 3 | 5 | 3 | 4 | 2 | 2 | 1 | 4 | 3 | 2 | 3 | 2 | 2 | 2 |
| 30 | 4 | 5 | 5 | 5 | 5 | 5 | 5 | 3 | 4 | 3 | 3 | 3 | 2 | 2 |
| 31** | | | | | | | | | | | | | | |
| 32 | 4 | 5 | 5 | 5 | 5 | 5 | 4 | 3 | 3 | 2 | 3 | 3 | 2 | 2 |
| 33 | 3 | 5 | 5 | 4 | 4 | 2 | 1 | 2 | 2 | 2 | 2 | 2 | 2 | 1 |
| 34** | | | | | | | | | | | | | | |
| 35 | 2 | 3 | 3 | 4 | 2 | 1 | 1 | 2 | 2 | 2 | 2 | 2 | 2 | 1 |

*Tested as a mixture containing a substantial amount of the compound of Ex. 4.
**Tested as a mixture.

TEST 3

Multiple-species Greenhouse test

In general, the test method was the same as the method of the test above. Various compounds were tested preemergence and postemergence at different application rates which are indicated in the tables below. A number of additional weed and crop species were used in the preemergence tests as is shown in the table. Typical results were as follows.

Table 3

| Compound of Example No. | Rate of Appln. kg./ha. | Corn | Cotton | Soybean | Wheat | Alfalfa | Sugar Beet | Rice | Cucumber | Tomato | Barnyard grass | Lambsquarter | Large Crabgrass | Mustard | Pigweed | Foxtail | Wild Oat | Velvetleaf | Jimsonweed | Morningglory | Zinnia |
|---|---|---|---|---|---|---|---|---|---|---|---|---|---|---|---|---|---|---|---|---|---|
| 1 | 0.28 | 4 | 1 | 4 | 4 | 5 | 4 | 2 | 2 | 4 | 4 | 4 | 5 | 5 | 4 | 4 | 3 | 4 | 4 | 3 | 3 |
| 2* | 1.1 | 4 | 1 | 4 | 4 | 5 | 5 | 3 | 4 | 4 | 5 | 5 | 5 | 5 | 5 | 5 | 4 | 5 | 5 | 4 | 4 |
| 3 | 0.56 | 3 | 1 | 2 | 4 | 4 | 2 | 1 | 1 | 2 | 3 | 3 | 5 | 5 | 4 | 4 | 1 | 3 | 2 | 2 | 2 |
| 4 | 2.2 | 3 | 1 | 2 | 3 | 5 | 5 | 2 | 2 | 4 | 4 | 5 | 5 | 5 | 5 | 5 | 2 | 5 | 4 | 3 | 2 |
|  | 0.56 | 2 | 1 | 2 | 3 | 2 | 3 | 1 | 2 | 2 | 3 | 4 | 5 | 5 | 2 | 5 | 2 | 2 | 4 | 2 | 2 |
|  | 2.2 | 4 | 1 | 3 | 5 | 4 | 5 | 2 | 3 | 5 | 5 | 4 | 5 | 5 | 5 | 5 | 3 | 5 | 4 | 4 | 4 |
| 5* | 2.2 | 3 | 1 | 2 | 4 | 4 | 4 | 3 | 2 | 5 | 4 | 4 | 5 | 5 | 4 | 5 | 4 | 5 | 4 | 4 | 4 |
| 7 | 1.1 | 2 | 1 | 2 | 4 | 4 | 4 | 2 | 2 | 4 | 4 | 4 | 3 | 3 | 2 | 4 | 3 | 4 | 4 | 3 | 2 |
| 8 | 0.14 | 3 | 1 | 2 | 3 | 5 | 4 | 1 | 2 | 3 | 4 | 4 | 3 | 3 | 4 | 3 | 3 | 4 | 3 | 2 | 2 |
| 8** | 0.14 | 2 | 1 | 2 | 2 | 3 | 4 | 1 | 1 | 2 | 3 | 2 | 3 | 2 | 3 | 4 | 2 | 3 | 2 | 2 | 1 |
| 9 | 0.56 | 2 | 1 | 2 | 2 | 2 | 3 | 1 | 1 | 3 | 3 | 3 | 4 | 3 | 4 | 3 | 2 | 2 | 2 | 2 | 1 |
| 10 | 1.1 | 3 | 1 | 3 | 3 | 4 | 3 | 2 | 1 | 3 | 4 | 4 | 5 | 4 | 4 | 4 | 4 | 4 | 2 | 2 | 2 |
| 11 | 2.2 | 2 | 1 | | 2 | 3 | 3 | 1 | 1 | 2 | 4 | 4 | 4 | 2 | 4 | 4 | 2 | 2 | 1 | 1 | 1 |
| 12 | 0.56 | 2 | 1 | | 2 | 4 | 4 | 1 | 1 | 3 | 4 | 3 | 5 | 2 | 3 | 4 | 3 | 2 | 1 | 1 | 1 |
| 13 | 2.2 | 3 | 1 | | 2 | 3 | 5 | 2 | 1 | 4 | 4 | 5 | 5 | 2 | 4 | 5 | 3 | 3 | 2 | 1 | 2 |
| 13a** | 2.2 | 3 | 1 | 1 | 2 | 2 | 3 | 1 | 2 | 3 | 4 | 5 | 4 | 2 | 4 | 4 | 2 | 3 | 3 | 2 | 2 |
| 14 | 2.2 | 3 | 1 | | 1 | 2 | 4 | 1 | 1 | 4 | 4 | 4 | 5 | 2 | 5 | 5 | 1 | 3 | 2 | 2 | 2 |
| 15** | 0.56 | 3 | 1 | 1 | 2 | 4 | 2 | 1 | 2 | 2 | 3 | 5 | 4 | 2 | 5 | 5 | 3 | 2 | 2 | 1 | 1 |
| 16 | 2.2 | 3 | 1 | 1 | 2 | 4 | 2 | 1 | 1 | 2 | 3 | 3 | 4 | 2 | 5 | 3 | 1 | 2 | 2 | 1 | 2 |
| 18 | 1.1 | 2 | 1 | 2 | 2 | 2 | 5 | 3 | 3 | 4 | 3 | 5 | 5 | 3 | 5 | 4 | 4 | 5 | 2 | 2 | 2 |
| 19 | 2.2 | 2 | 2 | 3 | 3 | 3 | 4 | 2 | 3 | 4 | 4 | 4 | 4 | 3 | 5 | 4 | 3 | 3 | 2 | 4 | 3 |
| 20 | 1.1 | 2 | 1 | 2 | 3 | 3 | 3 | 1 | 1 | 2 | 3 | 4 | 5 | 3 | 2 | 3 | 2 | 4 | 2 | 2 | 2 |
| 21 | 2.2 | 1 | 2 | 1 | 2 | 2 | 3 | 2 | 2 | 3 | 3 | 2 | 3 | 2 | 2 | 3 | 1 | 3 | 3 | 1 | 2 |
| 22 | 1.1 | 3 | 1 | 1 | 2 | 4 | 5 | 2 | 1 | 3 | 4 | 5 | 5 | 3 | 4 | 4 | 2 | 3 | 2 | 2 | 1 |
| 23 | | | | | | | | | | | | | | | | | | | | | |
| 24** | | | | | | | | | | | | | | | | | | | | | |
| 25 | | | | | | | | | | | | | | | | | | | | | |
| 26 | | | | | | | | | | | | | | | | | | | | | |
| 27** | 1.1 | 1 | 1 | 1 | 3 | 3 | 3 | 1 | 1 | 2 | 3 | 4 | 5 | 3 | 4 | 4 | 1 | 2 | 1 | 2 | 1 |
| 28 | | | | | | | | | | | | | | | | | | | | | |
| 29 | | | | | | | | | | | | | | | | | | | | | |

*Tested as a mixture containing a substantial amount of the compound of Ex. 4.
**Tested as a mixture.

Table 4

| Compound of Example No. | Rate of Appln. kg./ha. | Postemergence | | | | | | |
|---|---|---|---|---|---|---|---|---|
| | | Corn | Large Crabgrass | Pigweed | Foxtail | Velvetleaf | Morning-glory | Zinnia |
| 1 ⟍ ** 2 ╱ | 1.1 | 3 | 4 | 3 | 3 | 2 | 2 | 2 |
| | 4.5 | 4 | 4 | 3 | 4 | 3 | 2 | 2 |
| 3 | 1.1 | 3 | 3 | 2 | 2 | 2 | 2 | 2 |
| 3 | 4.5 | 3 | 4 | 3 | 3 | 3 | 2 | 2 |

*Tested as a mixture.

TEST 4

Yellow Nutsedge Test

Typical compounds were evaluated in the greenhouse against yellow nutsedge in a test method which followed in general the method of Test 1, except that the acetone-ethanol solution contained about 1.5 g./100 ml. of the test compound. Both preemergence and postemergence tests of the compounds were made, and rates of from 0.28 to 9.0 kg./ha. were applied in some instances. The 1–5 rating scale was used in tests at 9.0 kg./ha., while tests at lower application rates were rated in percent control of the weed. The test compounds were incorporated in the soil for testing preemergence at rates below 9.0 kg./ha. The results of testing typical compounds are presented in the table below.

Table 5

| Compound of Experiment No. | Rate kg./ha. | Pre-emergence | Post-emergence |
|---|---|---|---|
| 1 ⟍ ╱ 2 | 9.0 | 5 | 4 |
| | 2.2 | 100% | 75% |
| 1 ⟍ ╱ 2 | 0.56 | 80% | 40% |
| | 0.28 | 70% | |
| 3 | 9.0 | 5 | 4 |
| 3 | 2.2 | 95% | 75% |
| 3 | 0.56 | 80% | 40% |
| 3 | 0.28 | 60% | |
| 6 | 9.0 | 2 | 2 |
| 7 | 9.0 | 5 | 4 |

*Tested as a mixture.

TEST 5

Broadleaf Weed Test

A number of typical compounds were tested in the greenhouse against broadleaf weeds which are representative of families of weeds which exhibit resistance to many known herbicides. The test method was generally the same as the method of Test 4, except that only preemergence surface applications of the compounds were made. All compounds were tested at 9.0 kg./ha. The 1–5 rating scale was used.

Table 6

| Compound of Example No. | Garden Huckleberry | Sicklepod | Common Ragweed | Prickly Sida |
|---|---|---|---|---|
| 1 ⟍ ╱ 2 | 5 | 5 | 5 | |
| 3 | 5 | 5 | 5 | |
| 6 | 3 | 3 | | 4 |
| 7 | 5 | 5 | 5 | |

*Tested as a mixture.

TEST 6

Fourteen-Species Test

This greenhouse test was performed to evaluate typical compounds of the invention against a number of crop and weed species. The compounds were tested at various rates as indicated in the table below. In all cases, the compounds were applied preemergence to the test plants and were either incorporated in the soil before the seeds were planted, or surface-applied after planting. In general, the formulation of the compounds and planting and observation of the test plants proceeded according to the method of Test 4, except that the compounds were dissolved in acetone-ethanol at 1 g./100 ml. concentration. A 0–10 rating scale was used, where 0 indicates normal plants, and 10 indicates dead plants or no emergence.

Table 7

| Compound of Ex. No. | Rate of Appln. | Corn | Foxtail Millet | Grain Sorghum | Wild Oat | Rice | Barnyard Grass | Wheat | Morning-glory | Soybean | Prickly sida | Cotton | Pigweed | Cucumber | Jimsonweed |
|---|---|---|---|---|---|---|---|---|---|---|---|---|---|---|---|
| Surface Applied | | | | | | | | | | | | | | | |
| 1 ⟍ ╱ 2 | 0.56 | 8 | 10 | 7 | 4 | 3 | 8.5 | 2 | 2 | 3 | 10 | 0 | 2 | 2 | 8 |
| | 2.2 | 9.5 | 10 | 9.5 | 8 | 4 | 10 | 8 | 10 | 6 | 10 | 0 | 10 | 10 | 10 |
| 3 | 0.56 | 7 | 9 | 3 | 2 | 2 | 7 | 0 | 2 | 0 | 8 | 0 | 0 | 0 | 3 |
| 3 | 2.2 | 8 | 10 | 9 | 4 | 3 | 10 | 5 | 5 | 6 | 10 | 0 | 3 | 3 | 10 |
| Incorporated | | | | | | | | | | | | | | | |
| 1 ⟍ ╱ 2 | 0.28 | 10 | 9 | 9.5 | 9.8 | 9.8 | 10 | 10 | 10 | 7 | 10 | 0 | 8 | 7 | 9.5 |
| | 1.1 | 10 | 10 | 10 | 10 | 10 | 10 | 10 | 10 | 10 | 10 | 0 | 10 | 10 | 10 |
| 3 | 0.56 | 8.5 | 8 | 8 | 7.5 | 6 | 9 | 9 | 3 | 4 | 4 | 0 | 2 | 2 | 6 |
| 3 | 2.2 | 10 | 10 | 10 | 10 | 9.8 | 10 | 10 | 8 | 8.5 | 10 | 0 | 7 | 10 | 9 |

*Tested as a mixture.

The broad-spectrum activity of the compounds of this invention is clearly illustrated by the above examples. The test results point up the efficacy of the compounds against annual grasses, the relatively easily-controlled broadleaves such as pigweed, and the more resistant broadleaves such as nightshades. Plant scientists will recognize that the exemplified activity of the compounds shows that the compounds are broadly effective against herbaceous weeds.

As the above test results demonstrate, an important embodiment of this invention is a method of reducing the vigor of unwanted herbaceous plants which comprises contacting the plants with an herbicidally-effective amount of one of the compounds described above. In some instances, as is clear from the test results, the whole population of the contacted plant is killed. In other instances, part of the plants are killed and part of them are injured, and in still other instances, none of the plants are killed but are merely injured by application of the compound. It will be understood that reducing the vigor of the unwanted plant population by injuring the individual plants, or by killing part and injuring part, is beneficial even though some part of the plant population survives application of the compound. The plants, the vigor of which has been reduced, are unusually susceptible to the stresses, such as disease, drought, lack of nutrients and so forth, which normally afflict plants.

Thus, the treated plants, even though they survive application of the compound, are likely to expire due to stress of the environment. Further, if the treated plants are growing in cropland, the crop, growing normally, tends to shade out the treated plants of reduced vigor. The crop, therefore, has a great advantage over the treated unwanted plants in the competition for nutrients and sunlight. Still further, when the treated plants are growing in fallow land, or industrial property which is desired to be bare, the fact that their vigor is reduced necessarily tends to minimize the treated plants' consumption of water and nutrients, and also minimizes the fire hazard and nuisance which the plants present.

The compounds are herbicidally effective when applied both preemergence and postemergence. Thus, they can be applied to the soil to kill and injure weeds by soil contact when the weed seeds are germinating and emerging, and can also be used to kill and injure growing weeds by direct contact with the exposed portions of the weeds. Preemergence application of the compounds, wherein the unwanted herbaceous plants are contacted with the compound through application to the soil, is preferred. Seeds of unwanted plants, which are contacted with the compounds by soil application, are here regarded as plants.

Preemergence applications of the compounds are effective, as the examples show, whether the compounds are applied to the surface of the soil or are incorporated in the soil.

The preferred compounds of this invention, which are also the compounds with which the herbicidal method is preferably carried out, are the following.

2,3-dihydro-1-methyl-3-(3-methylphenyl)-5-phenyl-4(1H)-pyridinone.

2,3-dihydro-1-methyl-5-(3-methylphenyl)-3-phenyl-4(1H)-pyridinone.

2,3-dihydro-1-methyl-3-phenyl-5-(3-trifluoromethylphenyl)-4(1H)-pyridinone.

2,3-dihydro-1-methyl-5-phenyl-3-(3-trifluoromethylphenyl)-4(1H)-pyridinone.

2,3-dihydro-3-(4-fluorophenyl)-1-methyl-5-(3-trifluoromethylphenyl)-4(1H)-pyridinone.

2,3-dihydro-5-(4-fluorophenyl)-1-methyl-3-(3-trifluoromethylphenyl)-4(1H)-pyridinone.

3-(4-chlorophenyl)-2,3-dihydro-1-methyl-5-(3-trifluoromethylphenyl)-4(1H)-pyridinone.

1-methyl-3-phenyl-5-(3-trifluoromethylphenyl)-4-piperidinone.

As the examples above illustrate, the compounds are acceptably safe to a number of crops, such as peanuts, soybean, sorghum, wheat and rice when applied at proper rates and at appropriate times. It will be noted that the compounds are particularly and notably harmless to cotton in the exemplified experiments. Because of the safety with which this crop may be treated with the compounds, the use of the method to reduce the vigor of unwanted plants in cotton cropland is a preferred embodiment of the invention.

The best application rate of a given compound of the invention for the control of a given plant varies, of course, depending upon the method of compound application, climate, soil texture, water and organic matter contents of the soil and other factors known to those skilled in plant science. It will be found, however, that the optimum application rate is in the range of from about 0.25 to about 20 kg./ha. in virtually every case. The optimum rates will usually be found to be within the preferred range of from about 1 to about 10 kg./ha.

The time when the compounds should be applied to the soil or the unwanted plants is widely variable, since the compounds are effective both preemergence and postemergence. At least some control will result from application of the compounds at any time when plants are growing or germinating. They may also be applied to the soil during a dormant season to kill weeds germinating during the following warm season.

When the compounds are used for weed control in an annual crop, it is usually best to apply a preemergence application of the compound to the soil at the time the crop is being planted. If the compound is to be soil incorporated, it will usually be applied and incorporated immediately before planting. If it is to be surface applied, it is usually simplest to apply the compound immediately after planting.

The compounds are applied to the soil or to emerged plants in the manners usual in agriculture. They may be applied to the soil in the form of either water-dispersed or granular formulations, the preparation of which will be discussed below. Usually, water-dispersed formulations will be used for the application of the compounds to emerged weeds. The formulations are applied with any of the many types of sprayers and granular applicators which are in wide use for the distribution of agricultural chemicals over soil or standing vegetation. When a compound is to be soil-incorporated, any of the usual soil incorporation equipment, such as the disc harrow, the power-driven rotary hoe and the like, are effective.

The compounds are useful for the control of aquatic weeds, as well as terrestrial undesired plants. Such aquatic weeds as duckweed, water milfoil, hydrilla and the like are controlled when the compounds are dispersed in the infested water at concentrations in the range of from about 0.1 to about 10 p.p.m. by weight. The compounds are applied to water in the form of the same types of herbicidal compositions used for other herbicidal uses.

The compounds are normally used in the practice of the method of this invention in the form of the herbicidal compositions which are an important embodiment of the invention. An herbicidal composition of this invention comprises a compound useful in the method of the invention and an inert carrier. In general, the compositions are formulated in the manners usual in agricultural chemistry, and are novel only because of the vital presence of the herbicidal compound.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier and surfactants. The concentration of the compound is usually from about 10 percent to about 90 percent. The inert carrier is usually chosen from among the attapulgite clays, the kaolin clays, the montmorillonite clays, the diatomaceous earths or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable and convenient.

I claim:

1. A method of reducing the vigor of unwanted herbaceous plants which comprises contacting the plants with an herbicidally-effective amount of a compound of the formula

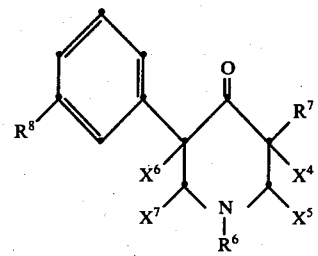

wherein
R$^6$ represents C$_1$-C$_3$ alkyl, C$_2$-C$_3$ alkenyl or propargyl;
R$^7$ represents hydrogen, phenoxy, phenylthio, C$_1$-C$_4$ alkyl, C$_1$-C$_4$ alkoxy, C$_1$-C$_4$ alkylthio, phenyl or phenyl monosubstituted with chloro, bromo, fluoro, trifluoromethyl, C$_1$-C$_3$ alkyl or C$_1$-C$_3$ alkoxy;
R$^8$ represents chloro, bromo, fluoro, trifluoromethyl, C$_1$-C$_3$ alkyl or C$_1$-C$_3$ alkoxy;
each of X$^4$ and X$^5$ represents hydrogen, or X$^4$ and X$^5$ combine to form a carbon-carbon bond;
each of X$^6$ and X$^7$ represents hydrogen, or X$^6$ and X$^7$ combine to form a carbon-carbon bond;
provided that at least one of (X$^4$ and X$^5$) and (X$^6$ and X$^7$) form a bond.

2. A method of claim 1 wherein the amount of the compound is from about 0.25 to about 20 kg./ha.

3. A method of claim 2 wherein the amount of the compound is from about 1 to about 10 kg./ha.

4. A method of claim 2 wherein the contacting is preemergence.

5. A method of claim 2 wherein the plants are in cotton cropland.

6. A method of claim 1 wherein R$^6$ represents alkyl or alkenyl.

7. A method of claim 6 wherein R$^7$ represents hydrogen, alkyl, phenyl or phenyl monosubstituted with chloro, bromo, fluoro, trifluoromethyl, methyl or methoxy.

8. A method of claim 7 wherein R$^8$ represents chloro, bromo, fluoro, trifluoromethyl, methyl or methoxy.

9. The method of claim 8 wherein the compound is 2,3-dihydro-1-methyl-3-(3-methylphenyl)-5-phenyl-4(1H)-pyridinone.

10. The method of claim 8 wherein the compound is 2,3-dihydro-1-methyl-5-(3-methylphenyl)-3-phenyl-4(1H)-pyridinone.

11. The method of claim 8 wherein the compound is 2,3-dihydro-1-methyl-3-phenyl-5-(3-trifluoromethylphenyl)-4(1H)-pyridinone.

12. The method of claim 8 wherein the compound is 2,3-dihydro-1-methyl-5-phenyl-3-(3-trifluoromethylphenyl)-4(1H)-pyridinone.

13. The method of claim 8 wherein the compound is 2,3-dihydro-3-(4-fluorophenyl)-1-methyl-5-(3-trifluoromethylphenyl)-4(1H)-pyridinone.

14. The method of claim 8 wherein the compound is 2,3-dihydro-5-(4-fluorophenyl)-1-methyl-3-(3-trifluoromethylphenyl)-4(1H)-pyridinone.

15. The method of claim 8 wherein the compound is 3-(4-chlorophenyl)-2,3-dihydro-1-methyl-5-(3-trifluoromethylphenyl)-4(1H)-pyridinone.

16. A compound of the formula

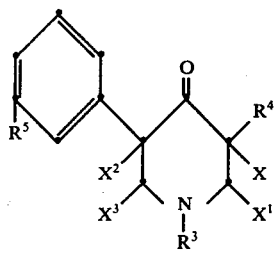

$R^3$ represents $C_1$-$C_3$ alkyl, $C_2$-$C_3$ alkenyl or propargyl;

$R^4$ represents hydrogen, phenoxy, phenylthio, $C_1$-$C_4$ alkyl, $C_1$-$C_4$ alkoxy, $C_1$-$C_4$ alkylthio, phenyl or phenyl monosubstituted with chloro, bromo, fluoro, trifluoromethyl, $C_1$-$C_3$ alkyl or $C_1$-$C_3$ alkoxy;

$R^5$ represents chloro, bromo, fluoro, trifluoromethyl, $C_1$-$C_3$ alkyl or $C_1$-$C_3$ alkoxy;

either X and $X^1$ combine to form a carbon-carbon bond and $X^2$ and $X^3$ represent hydrogen atoms, or X and $X^1$ represent hydrogen atoms and $X^2$ and $X^3$ combine to form a carbon-carbon bond.

17. A compound of claim 16 wherein $R^3$ represents alkyl or alkenyl.

18. A compound of claim 17 wherein $R^4$ represents hydrogen, alkyl, phenyl or phenyl monosubstituted with chloro, bromo, fluoro, trifluoromethyl, methyl or methoxy.

19. A compound of claim 17 wherein $R^5$ represents chloro, bromo, fluoro, trifluoromethyl, methyl or methoxy.

20. The compound of claim 19 which is 2,3-dihydro-1-methyl-3-(3-methylphenyl)-5-phenyl-4(1H)-pyridinone.

21. The compound of claim 19 which is 2,3-dihydro-1-methyl-5-(3-methylphenyl)-3-phenyl-4(1H)-pyridinone.

22. The compound of claim 19 which is 2,3-dihydro-1-methyl-3-phenyl-5-(3-trifluoromethylphenyl)-4(1H)-pyridinone.

23. The compound of claim 19 which is 2,3-dihydro-1-methyl-5-phenyl-3-(3-trifluoromethylphenyl)-4(1H)-pyridinone.

24. The compound of claim 19 which is 2,3-dihydro-3-(4-fluorophenyl)-1-methyl-5-(3-trifluoromethylphenyl)-4(1H)-pyridinone.

25. The compound of claim 19 which is 2,3-dihydro-5-(4-fluorophenyl)-1-methyl-3-(3-trifluoromethylphenyl)-4(1H)-pyridinone.

26. The compound of claim 19 which is 3-(4-chlorophenyl)-2,3-dihydro-1-methyl-5-(3-trifluoromethylphenyl)-4(1H)-pyridinone.

27. An herbicidal composition which comprises an inert carrier and a compound of the formula

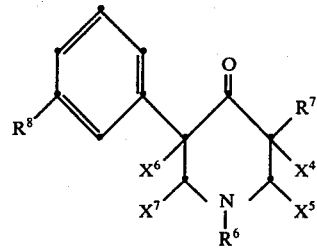

wherein $R^6$ represents $C_1$-$C_3$ alkyl, $C_2$-$C_3$ alkenyl or propargyl;

$R^7$ represents hydrogen, phenoxy, phenylthio, $C_1$-$C_4$ alkyl, $C_1$-$C_4$ alkoxy, $C_1$-$C_4$ alkylthio, phenyl or phenyl monosubstituted with chloro, bromo, fluoro, trifluoromethyl, $C_1$-$C_3$ alkyl or $C_1$-$C_3$ alkoxy;

$R^8$ represents chloro, bromo, fluoro, trifluoromethyl, $C_1$-$C_3$ alkyl or $C_1$-$C_3$ alkoxy;

each of $X^4$ and $X^5$ represents hydrogen, or $X^4$ and $X^5$ combine to form a carbon-carbon bond;

each of $X^6$ and $X^7$ represents hydrogen, or $X^6$ and $X^7$ combine to form a carbon-carbon bond;

provided that at least one of ($X^4$ and $X^5$) and ($X^6$ and $X^7$) form a bond.

28. A composition of claim 27 wherein $R^6$ represents alkyl or alkenyl.

29. A composition of claim 28 wherein $R^7$ represents hydrogen, alkyl, phenyl or phenyl monosubstituted with chloro, bromo, fluoro, trifluoromethyl, methyl or methoxy.

30. A composition of claim 29 wherein $R^8$ represents chloro, bromo, fluoro, trifluoromethyl, methyl or methoxy.

31. The composition of claim 30 wherein the compound is 2,3-dihydro-1-methyl-3-(3-methylphenyl)-5-phenyl-4(1H)-pyridinone.

32. The composition of claim 30 wherein the compound is 2,3-dihydro-1-methyl-5-(3-methylphenyl)-3-phenyl-4(1H)-pyridinone.

33. The composition of claim 30 wherein the compound is 2,3-dihydro-1-methyl-3-phenyl-5-(3-trifluoromethylphenyl)-4(1H)-pyridinone.

34. The composition of claim 30 wherein the compound is 2,3-dihydro-1-methyl-5-phenyl-3-(3-trifluoromethylphenyl)-4(1H)-pyridinone.

35. The composition of claim 30 wherein the compound is 2,3-dihydro-3-(4-fluorophenyl)-1-methyl-5-(3-trifluoromethylphenyl)-4(1H)-pyridinone.

36. The composition of claim 30 wherein the compound is 2,3-dihydro-5-(4-fluorophenyl)-1-methyl-3-(3-trifluoromethylphenyl)-4(1H)-pyridinone.

37. The composition of claim 30 wherein the compound is 3-(4-chlorophenyl)-2,3-dihydro-1-methyl-5-(3-trifluoromethylphenyl)-4(1H)-pyridinone.

* * * * *

UNITED STATES PATENT OFFICE
CERTIFICATE OF CORRECTION

Patent No. 4,102,669          Dated   July 25, 1978

Inventor(s) Harold Mellon Taylor

It is certified that error appears in the above-identified patent and that said Letters Patent are hereby corrected as shown below:

Column 9, line 68:   "4(1H9-" should read --4(1H)--.

Column 11, line 4:   "(31 -methylphenyl)" should read --(3-methylphenyl)--.

Column 11, line 6:   "propargyl4" should read --propargyl-4--.

Column 11, line 40:  "isopropenyl-31" should read --isopropenyl-3--.

Column 11, line 52:  "4(1)" should read --4(1H)--.

Signed and Sealed this

Eighth Day of May 1979

[SEAL]

Attest:

RUTH C. MASON
Attesting Officer

DONALD W. BANNER
Commissioner of Patents and Trademarks